(12) United States Patent
Brunsvold et al.

(10) Patent No.: US 11,350,925 B2
(45) Date of Patent: Jun. 7, 2022

(54) SURGICAL BUTTON INSERTER SYSTEM AND METHOD

(71) Applicant: Parcus Medical LLC, Sarasota, FL (US)

(72) Inventors: Mark D. Brunsvold, Sarasota, FL (US); Barton W. Bracy, Orlando, FL (US); Joel Harshbarger, Sarasota, FL (US)

(73) Assignee: PARCUS MEDICAL LLC, Sarasota, FL (US)

( * ) Notice: Subject to any disclaimer, the term of this patent is extended or adjusted under 35 U.S.C. 154(b) by 0 days.

(21) Appl. No.: 17/380,816

(22) Filed: Jul. 20, 2021

(65) Prior Publication Data

US 2021/0346008 A1 Nov. 11, 2021

Related U.S. Application Data

(60) Continuation of application No. 17/018,957, filed on Sep. 11, 2020, now Pat. No. 11,064,993, which is a division of application No. 16/580,348, filed on Sep. 24, 2019, now Pat. No. 10,772,619.

(60) Provisional application No. 62/738,295, filed on Sep. 28, 2018.

(51) Int. Cl.
*A61B 17/04* (2006.01)

(52) U.S. Cl.
CPC .. *A61B 17/0401* (2013.01); *A61B 2017/0404* (2013.01); *A61B 2017/0409* (2013.01); *A61B 2017/0414* (2013.01)

(58) Field of Classification Search
CPC ........ A61B 17/0401; A61B 2017/0404; A61B 2017/0409; A61B 2017/0403; A61B 2017/0414
See application file for complete search history.

(56) References Cited

U.S. PATENT DOCUMENTS

| 5,843,127 | A | 12/1998 | Li |
| 5,928,244 | A | 7/1999 | Tovey et al. |
| 6,161,999 | A * | 12/2000 | Kaye .................. F16B 13/0808 411/344 |
| 6,171,310 | B1 | 1/2001 | Giordano et al. |
| 6,451,030 | B2 | 9/2002 | Li et al. |

(Continued)

*Primary Examiner* — Dianne Dornbusch
(74) *Attorney, Agent, or Firm* — Fox Rothschild LLP

(57) ABSTRACT

A button inserter apparatus for the insertion of a surgical button includes an inserter handle and an elongated inserter shaft connected at one end to the inserter handle. An inserter head is connected to the inserter shaft at an end opposite to the inserter handle. The inserter head includes opposing engagement projections for engaging and retaining a surgical button there between. One of the engagement projections is longitudinally movable relative to the other of the engagement projections. A button engage and release assembly extends from the inserter handle to the inserter head, and selectively prevents relative longitudinal movement between the engagement projections, and selectively permits relative movement of the engagement projections and thereby release of the surgical button. The engage and release assembly is operable from the inserter handle to cause relative longitudinal movement of the engagement projections and release of the surgical button. A surgical button and a method of inserting a surgical button are also disclosed.

11 Claims, 35 Drawing Sheets

(56) References Cited

U.S. PATENT DOCUMENTS

| | | | |
|---|---|---|---|
| 6,660,022 B1 | 12/2003 | Li et al. | |
| 7,736,108 B1 * | 6/2010 | Bruce | F16B 13/0808 411/346 |
| 8,491,598 B2 * | 7/2013 | Crook | A61F 2/4611 606/99 |
| 8,603,175 B2 * | 12/2013 | Thibodeau | A61F 2/4465 623/17.16 |
| 8,858,143 B2 | 10/2014 | Gaudron et al. | |
| 8,888,792 B2 | 11/2014 | Harris et al. | |
| 8,894,669 B2 | 11/2014 | Nering et al. | |
| 9,072,509 B2 | 7/2015 | Stoll, Jr. et al. | |
| 9,839,530 B2 | 12/2017 | Hawkins et al. | |
| 2005/0107807 A1 | 5/2005 | Nakao | |
| 2011/0125189 A1 | 5/2011 | Stoll, Jr. et al. | |
| 2011/0160856 A1 * | 6/2011 | Sinnott | A61F 2/0811 623/13.14 |
| 2012/0180291 A1 * | 7/2012 | Oren | A61B 17/0401 29/428 |
| 2012/0203249 A1 * | 8/2012 | Schmidt | A61F 2/0805 606/144 |
| 2013/0035720 A1 * | 2/2013 | Perriello | A61B 17/0401 606/232 |
| 2015/0196385 A1 * | 7/2015 | Kam | A61B 17/0401 623/13.14 |
| 2016/0302938 A1 * | 10/2016 | Hawkins | A61F 2/4611 |
| 2018/0085110 A1 * | 3/2018 | Earhart | A61B 17/0401 |
| 2018/0249998 A1 * | 9/2018 | Chavan | A61B 17/0487 |

\* cited by examiner

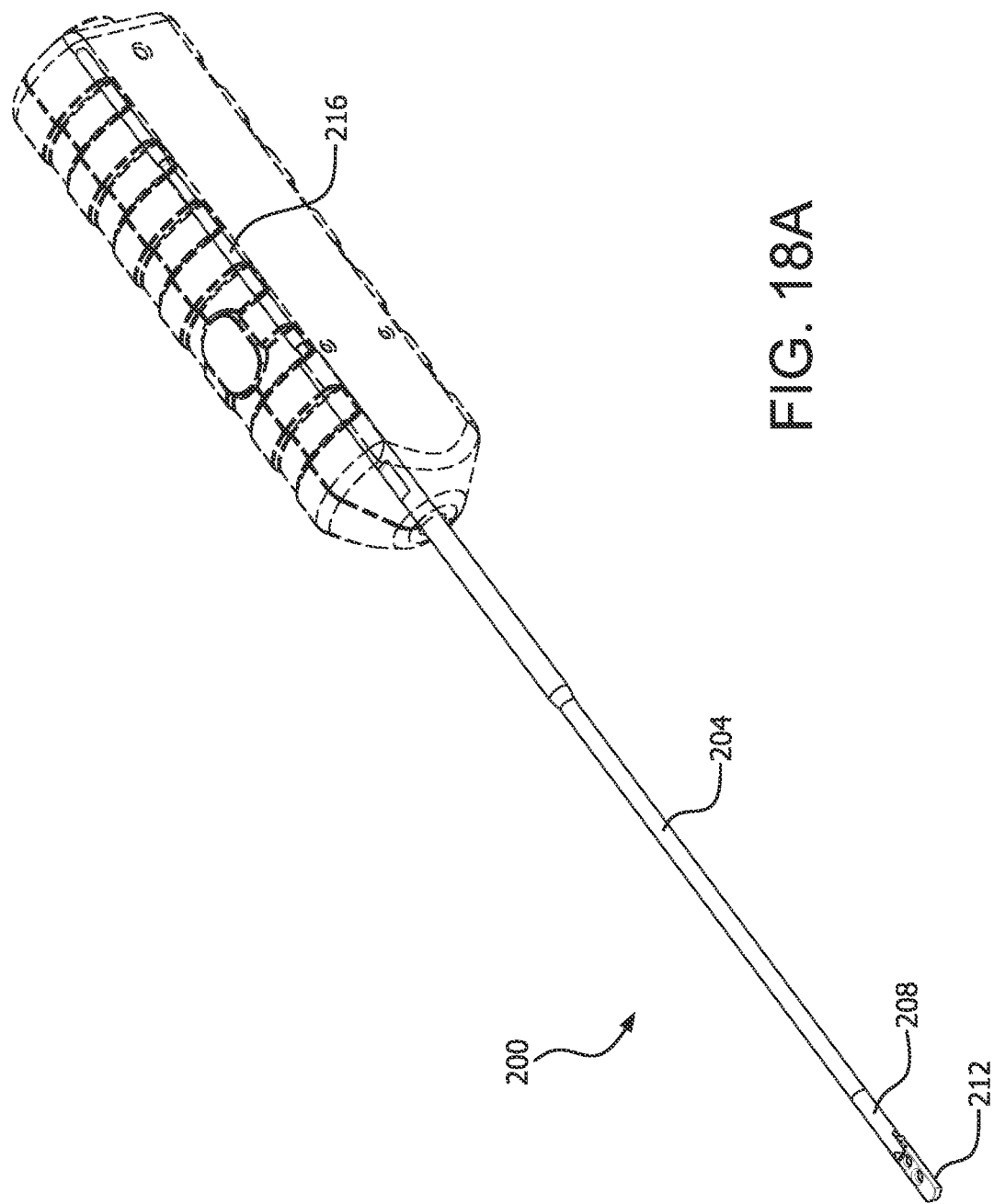

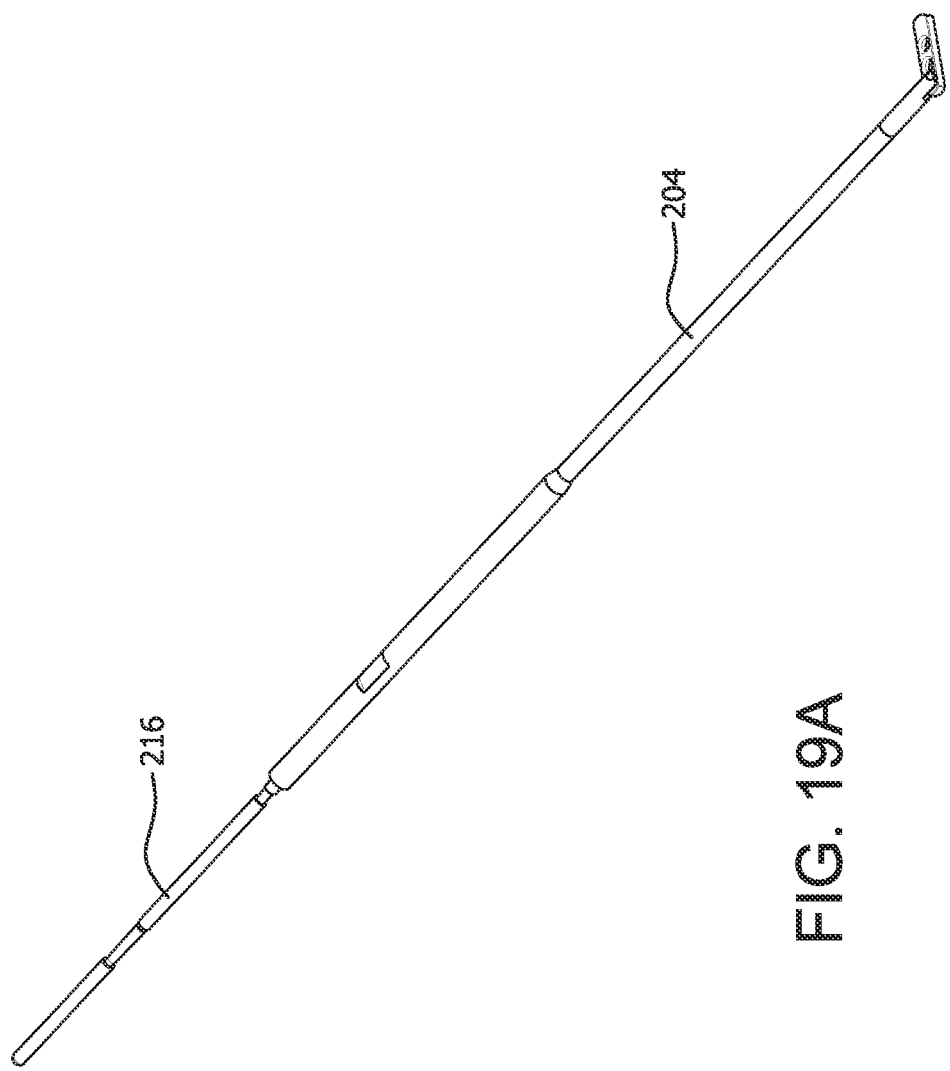

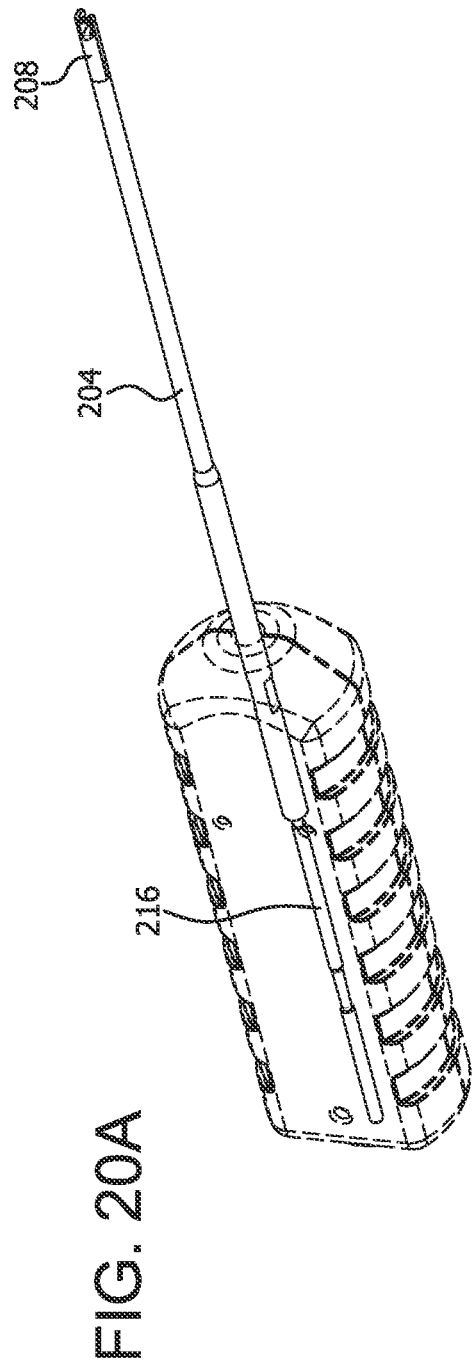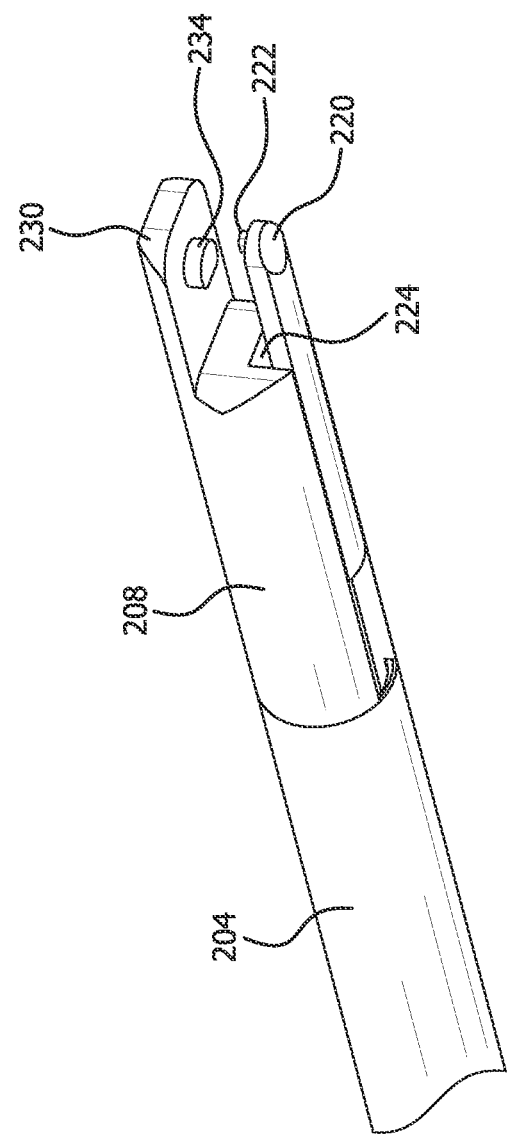
FIG. 20A
FIG. 20B

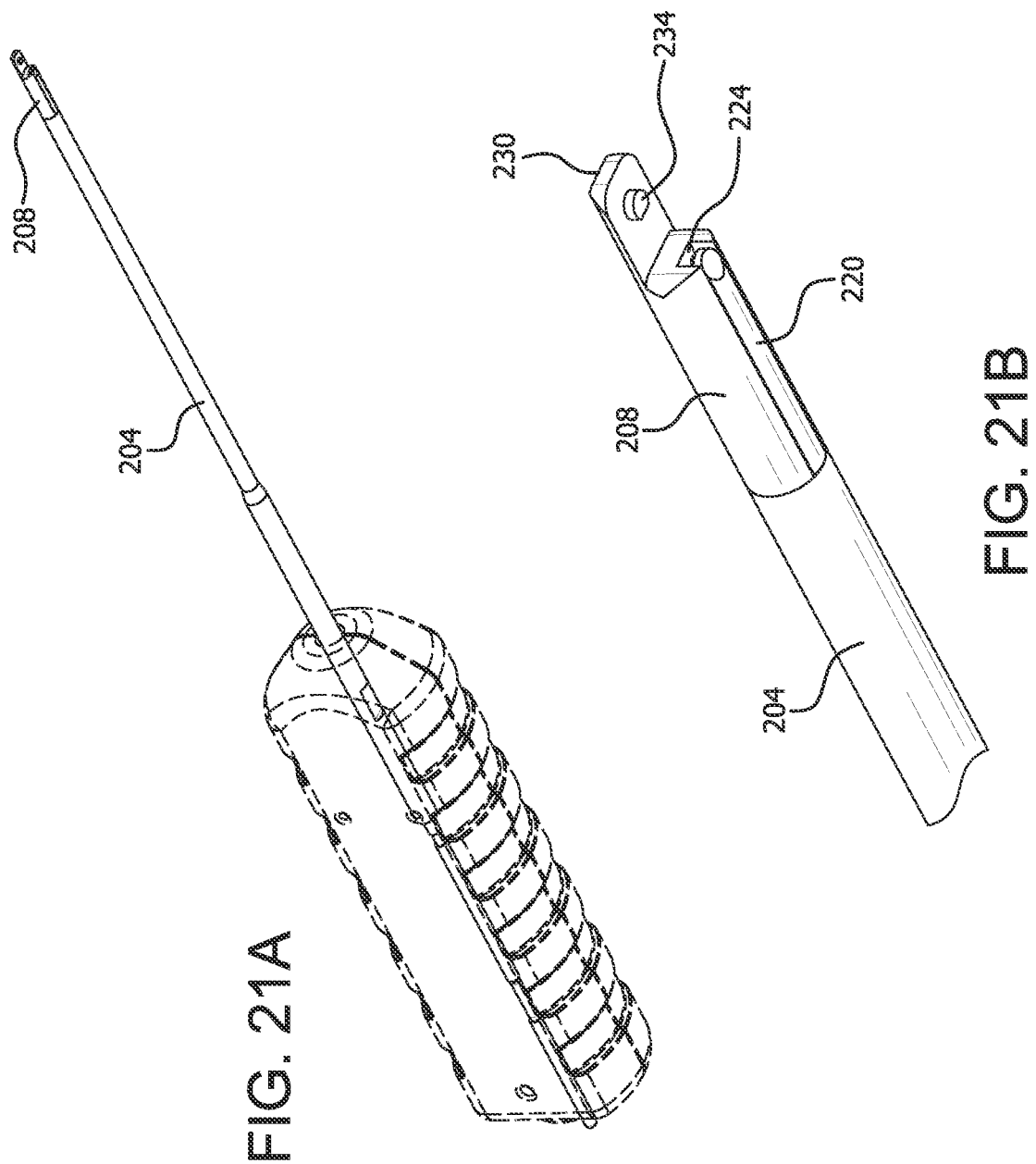

SURGICAL BUTTON INSERTER SYSTEM AND METHOD

CROSS-REFERENCE TO RELATED APPLICATIONS

This application is a continuation application of U.S. patent application Ser. No. 17/018,957 filed on Sep. 11, 2020, now U.S. Pat. No. 11,064,993 issued on Jul. 20, 2021, which is a divisional application of U.S. patent application Ser. No. 16/580,348 filed on Sep. 24, 2019, now U.S. Pat. No. 10,772,619 issued on Sep. 15, 2020, which claims priority to U.S. Provisional Application No. 62/738,295 filed on Sep. 28, 2018, entitled "BUTTON INSERTER AND METHOD", the entire disclosures of which are all incorporated herein by reference.

FIELD OF THE INVENTION

The present invention relates to surgical buttons and apparatus and methods for inserting surgical buttons into a patient.

BACKGROUND OF THE INVENTION

Surgical buttons are used to secure sutures and thereby other surgical items such as grafts to a body part. The use of surgical buttons to secure suture to bone presents particular challenges. A tunnel of significant length is sometimes formed through the bone. The elongated surgical button is dimensioned so as to fit through the tunnel axially, but is longer than the width of the tunnel such that when inserted through the tunnel and rotated the button will engage bone around the tunnel opening. Tension can then be applied to suture engaged to the button to secure the button and the suture in position.

The insertion of the surgical button through the tunnel followed by release and rotation of the button is difficult particularly in minimally invasive procedures where the dimensions of the surgical opening must be minimized. A grasper (plier) is used to grasp the button and push it into the tunnel in the body part. The grasper does not do a very good job of limiting rotation of the button during insertion. The surgeon must open the jaw to release the button in a very limited space. Attempts have been made to address these problems. One design utilized a threaded hole at the proximal end of the button and a threaded rod to engage and insert the button through the tunnel. The buttons are thin so the tapped hole must be small in diameter, and the threaded rod can break off during insertion of the button into the tunnel.

SUMMARY OF THE INVENTION

A button inserter apparatus for the insertion of a surgical button includes an inserter handle, an elongated inserter shaft connected at one end to the inserter handle, and an inserter head connected to the inserter shaft at an end opposite to the inserter handle. The inserter head can include opposing engagement projections for engaging and retaining a surgical button there between and in an axial orientation relative to the elongated shaft. One of the engagement projections can be longitudinally movable relative to the other of the engagement projections. A button engage and release assembly can extend from the inserter handle to the inserter head. The engage and release assembly prevents relative longitudinal movement between the engagement projections, and selectively permits relative movement of the engagement projections and thereby release of the surgical button. The engage and release assembly can be operable from the inserter handle to cause relative longitudinal movement of the engagement projections and release of the surgical button.

One of the engagement projections can be fixed relative to the inserter shaft, and can include a radially inward extending protrusion for engaging a radially extending cooperating depression in the surgical button. One of the engagement projections can include an axially-extending tongue for engaging an axially extending groove in the surgical button. The radially inward extending engagement protrusion can include a pin for engaging a transversely oriented aperture in the surgical button.

The engage and release assembly can include an elongated release member extending from the inserter head to the inserter handle, and can be selectively movable to axially move one of the engagement projections longitudinally and proximally to release the button. The engage and release assembly can further include a spring for selectively urging the release member axially and proximally to move the engagement projection. The engage and release assembly can include a detent for engaging the release member. The detent can be movable by an actuator in the inserter handle to disengage the release member to permit movement of an engagement projection and release of the surgical button.

One of the engagement projections can be axially movable relative to the inserter shaft and comprise an axially extending tongue having a radially inward extending cam protrusion for engaging a cooperating curved groove in the surgical button to laterally rotate the surgical button when the tongue and cam protrusion are moved axially. The other of the engagement projections can be fixed relative to the inserter shaft and comprise a radially inward extending protrusion for engaging a laterally extending cooperating depression in the surgical button.

A method of inserting a surgical button can include the step of providing a surgical button inserter device including an inserter handle, an elongated inserter shaft connected at one end to the inserter handle, and an inserter head connected to the inserter shaft at an end opposite to the inserter handle. The inserter head can include opposing engagement projections for engaging and retaining a surgical button there between and in an axial orientation relative to the elongated shaft. One of the engagement projections can be longitudinally movable relative to the other of the engagement projections, and one of the engagement projections can include an engagement protrusion. A button engage and release assembly can extend from the inserter handle to the inserter head. The engagement and release assembly prevents relative longitudinal movement between the engagement projections, and selectively permits relative longitudinal movement of the engagement projections and thereby release of the surgical button. The engage and release assembly can be operable from the inserter handle to cause relative longitudinal movement of the engagement projections and release of the surgical button. A surgical button can be provided which includes an engagement depression. The engagement protrusion can engage the engagement depression in the surgical button to retain the surgical button.

The surgical button can be secured between the engagement projections in an axial orientation relative to the inserter shaft, and with the engagement protrusion engaged to the engagement depression of the surgical button. The button inserter can be manipulated to position the surgical button in a target location. The button engage and release assembly can be manipulated to move one of the engagement projections longitudinally and to thereby release the surgical button.

At least one of the engagement projections can include an axially movable tongue longitudinally movable by the engage and release assembly to release the surgical button. The engagement depression can have a groove adapted to receive the tongue. The button engage and release assembly can be operated to move the axially movable tongue from a position in the groove of the surgical button to release the surgical button.

One of the engagement projections can include a radially inward extending protrusion for engaging a lateral cooperating depression in the surgical button. The method can include the step of manipulating the surgical button to remove the button from engagement with the lateral protrusion.

One of the engagement projections can be fixed relative to the inserter shaft, and can include a radially inward extending engagement protrusion for engaging a radially extending cooperating engagement depression in the surgical button. The other of the engagement projections can include an axially-extending tongue for engaging an axially extending groove in the surgical button. The method can include the steps of moving the axially-extending tongue longitudinally and proximally to release the surgical button, and manipulating the surgical button to remove the surgical button from the radially extending engagement protrusion.

One of the engagement projections can be axially movable relative to the inserter shaft and comprise an axially extending tongue having a radially inward extending cam protrusion for engaging a cooperating curved groove in the surgical button extending to a first elongated side of the surgical button. The method can include moving the axially extending tongue and cam protrusion to laterally rotate the surgical button when the tongue and cam protrusion are moved axially.

One of the engagement projections can be fixed relative to the inserter shaft and comprise a radially inward extending engagement protrusion. A transverse groove can be provided on a second button body face of the surgical button extending from a medial position to the first elongated side of the surgical button. The immovable engagement protrusion can be positioned in the medial position of the transverse groove. The method can include sliding the button off of the immovable engagement protrusion of the button inserter device after the button has been rotated.

A surgical button can include a button body with opposing button faces, and elongated sides and short sides, and comprising at least one suture opening extending from one of the button body faces to the other of the faces. The surgical button can further include at least one inserter engagement depression for receiving an engagement protrusion of a button inserter device. The engagement depression can include a medially positioned, axially extending depression extending to one of the short sides of the button body. The engagement depression can be a groove formed in one of the button body faces and extending medially and proximally to one of the button body short sides. The engagement depression can be transverse to the button body faces. The button can include a groove formed in one of the button body faces and extending medially and proximally to one of the button body short sides, and a medial transverse depression transverse to the button body faces. The transverse depression can have an axis that intersects the groove.

The inserter engagement depression can include a curved groove in the surgical button extending from a medial positon on a first button body face to a first elongated side of the surgical button. The surgical button can further include a transverse groove on a second button body face of the surgical button extending from a medial position to the first elongated side of the surgical button.

BRIEF DESCRIPTION OF THE DRAWINGS

There are shown in the drawings embodiments that are presently preferred it being understood that the invention is not limited to the arrangements and instrumentalities shown, wherein:

FIG. 18A is a perspective view, partially in phantom, of an alternative embodiment.

FIG. 19A is a perspective view of an inserter shaft of the alternative embodiment in a second mode of operation.

FIG. 20A is a perspective view, partially in phantom, of an alternative embodiment of a button inserter; FIG. 20B is a magnified view of an alternative inserter head.

FIG. 21A is a perspective view, partially in phantom of the alternative embodiment of FIG. 20A, in a second mode of operation; FIG. 21B is a magnified view of the alternative inserter head in the second mode of operation.

DETAILED DESCRIPTION OF THE INVENTION

Figure 1:
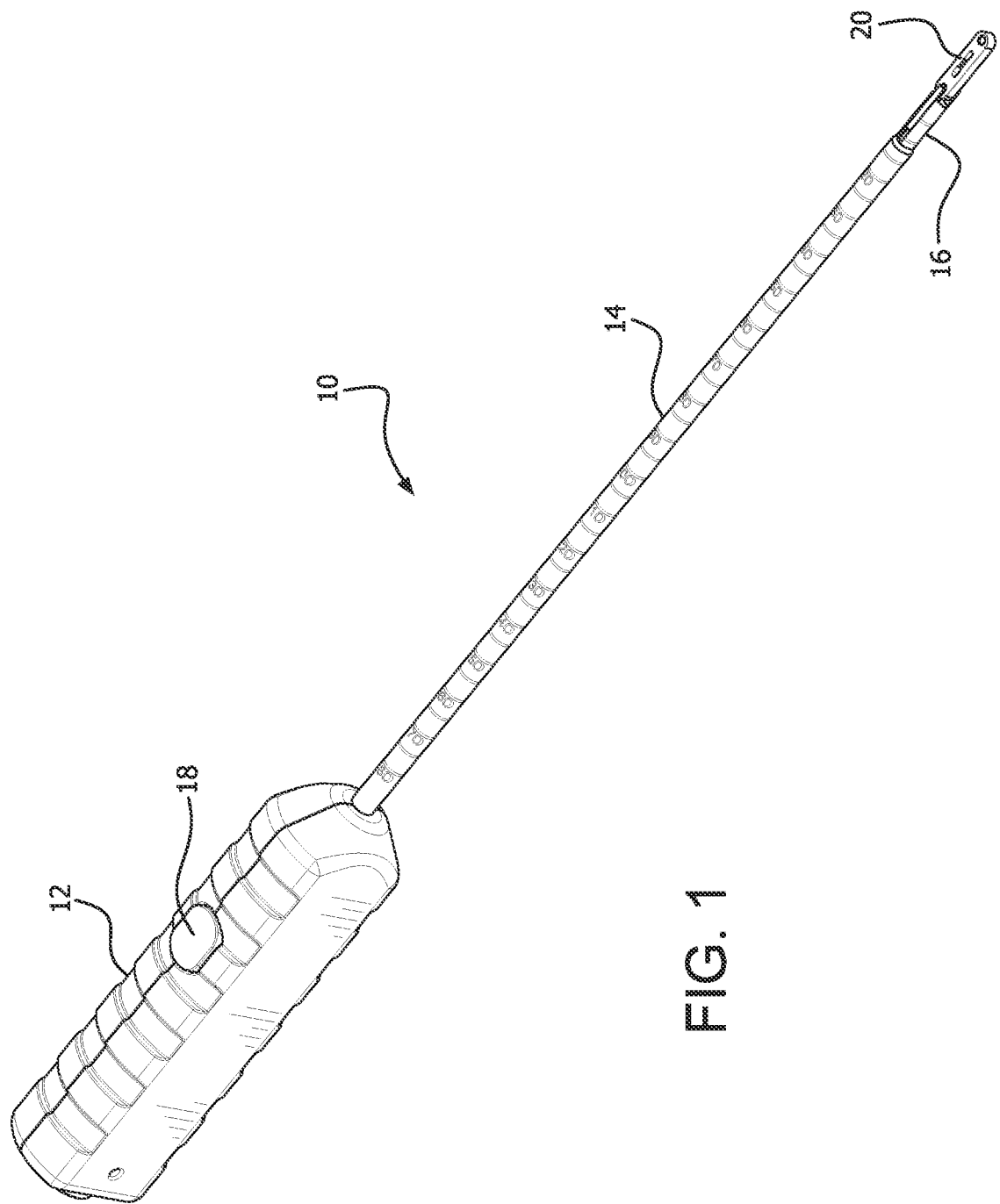
FIG. 1 is a a perspective view of a button inserter assembly according to the invention.

A button inserter apparatus for the insertion of a surgical button includes an inserter handle and an elongated inserter shaft connected at one end to the inserter handle. The inserter handle can have different sizes and shapes. An inserter head is connected to the inserter shaft at an end opposite to the inserter handle. The inserter head can be a connected piece or integrally formed with the inserter shaft. The inserter head includes opposing engagement projections for engaging and retaining a surgical button there between and in an axial orientation relative to the elongated shaft. One of the engagement projections is axially movable relative to the other of the engagement projections and the inserter shaft.

A button engage and release assembly extends from the inserter handle to the inserter head. The engage and release assembly prevents relative axial movement between the engagement projections, and selectively permits relative movement of the engagement projections and thereby release of the surgical button. The engage and release assembly is operable from the inserter handle to cause relative longitudinal movement of the engagement projections and release of the surgical button. The engage and release assembly can be mechanical, electrical such as a solenoid, or a combination of mechanical and electrical components.

One of the engagement projections can include an axially-extending tongue or other movable piece for engaging an axially extending groove or opening in the surgical button. The inserter shaft can be tubular, and the engage and release assembly can include an elongated release member extending from the inserter head to the inserter handle within the tubular inserter shaft. The elongated release member can be selectively movable to move one of the engagement projections axially and proximally to release the button. The engage and release assembly can include a spring for selectively urging the release member axially and proximally to move the engagement projection.

An actuator assembly is provided to selectively operate the release member. The actuator assembly can include a detent or key portion for engaging the release member. The key portion has a key opening with narrow and large opening portions. The key portion or detent is movable by the actuator assembly. The release member has a narrowed neck portion. In the secured position, the narrowed neck portion is engaged within the narrow part of the key opening, and the release member cannot move axially. In the released position, the key portion is moved such that the large key opening is aligned with the release member. The large key opening has a dimension larger than the diameter of the release member, thereby permitting passage and axial movement of the release member. The release member is operatively connected to the axially movable projection, and thereby axial movement of the release member will result in release of the button. Other designs for selectively engaging the release member are possible.

One of the engagement projections can be fixed relative to the inserter shaft. The fixed projection can include a radially inward extending protrusion for engaging a radially extending cooperating depression or aperture in the surgical button. The radially inward extending engagement protrusion can be a pin for engaging a transversely oriented aperture in the surgical button. The pin will releasably secure the button against unrestrained movement when the tongue or axially movable projection is retracted, where the button could otherwise move to an undesirable position. The pin will retain the button until manipulation as by a suture is performed by the surgeon. Other shapes and constructions for the radially inward extending protrusion and cooperating depression are possible.

A method of inserting a surgical button includes securing the surgical button between the engagement projections of the inserter head in an axial orientation relative to the inserter shaft, and with the radially inward extending engagement protrusion engaged to the engagement depression of the surgical button. The button inserter is manipulated to position the surgical button through the tunnel or opening to a target location. The inserter shaft and head can have a lateral dimension the is the same as that of the surgical button, or in one embodiment no more than 10% wider than the width of the surgical button, and can be narrower than the surgical button. The dimensions of the inserter shaft and inserter head provide that the button with the inserter head and inserter shaft are readily passed through the tunnel. The button engage and release assembly is operated to move one of the engagement projections longitudinally and to thereby release the surgical button. The button can then be manipulated to remove it from the pin, if a pin or other later protrusion is provided.

A surgical button for the invention includes a button body with opposing button faces, and elongated sides and short sides. The dimensions of the surgical button can vary. The surgical button commonly includes at least one suture opening extending from one of the button body faces to the other of the faces for threading of the suture to the button. The number and size and shape of such openings will vary depending on the use of the surgical button in the surgical procedure. The surgical button can have other or additional structure suitable for a surgical button.

The surgical button has at least one inserter engagement depression for receiving an axially movable engagement protrusion of the button inserter device. The engagement depression can be a medially positioned, axially extending depression extending to one of the short sides of the button body. The engagement depression can be a groove formed in a face of the surgical button, extending medially and proximally to one of the button body short sides which will be proximal when the button is secured to the inserter head. The engagement depression can be transverse to the button body faces. A medial transverse depression or aperture can be transverse to the button body faces. The radially inward extending, transverse depression or aperture can have an axis that intersects the groove.

There is shown in FIGS. 1-5 a button insertion assembly including a button inserter 10 and a surgical button 20. The button inserter 10 has a handle 12 and an elongated inserter shaft 14 terminating in a button inserter head 16. An actuator 18 is provided in the handle 12 for operation of the button inserter 10 as will be described.

Figure 2:
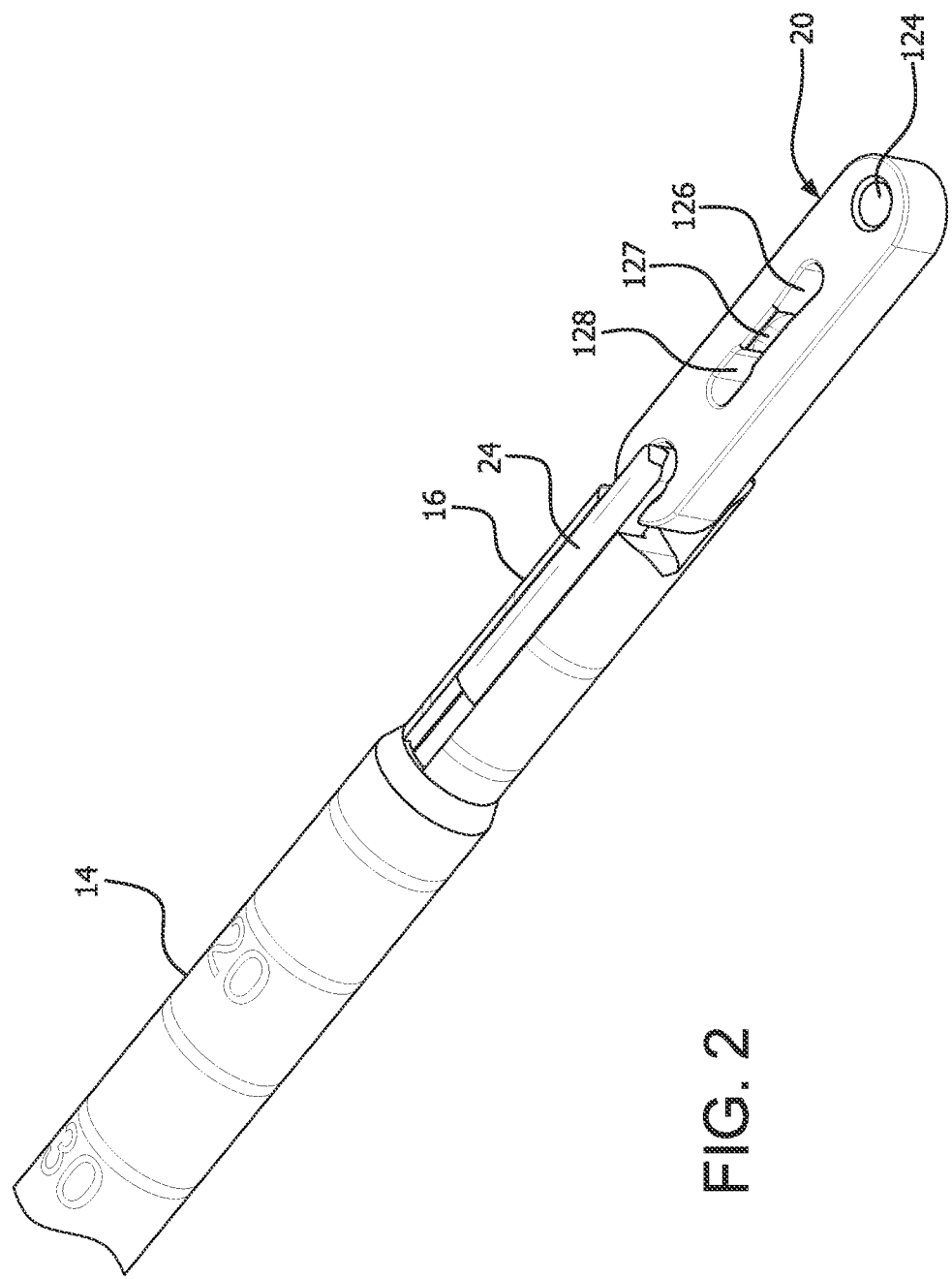
FIG. 2 is a perspective view of a button inserter head and surgical button in a secured position.

The surgical button 20 can be of any suitable shape, size, and design. As shown in FIG. 2, the surgical button can have suture openings 126 and 128 for threading a surgical suture, and a supporting bridge 127 for supporting the surgical suture in position. Other surgical button designs and structure are possible.

Figure 3:
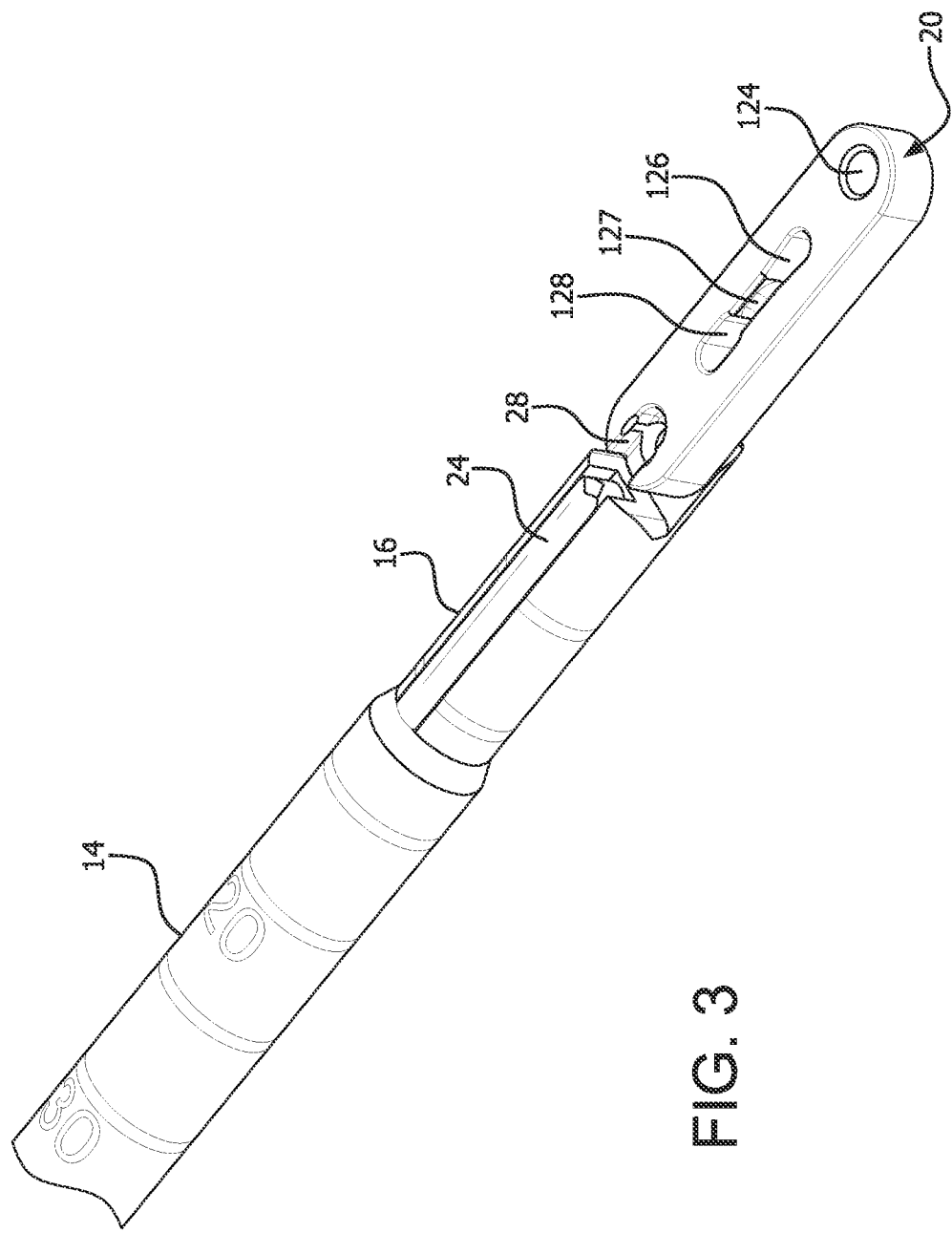
FIG. 3 is a perspective view of a button inserter head and surgical button in a partially released position.
Figure 4:
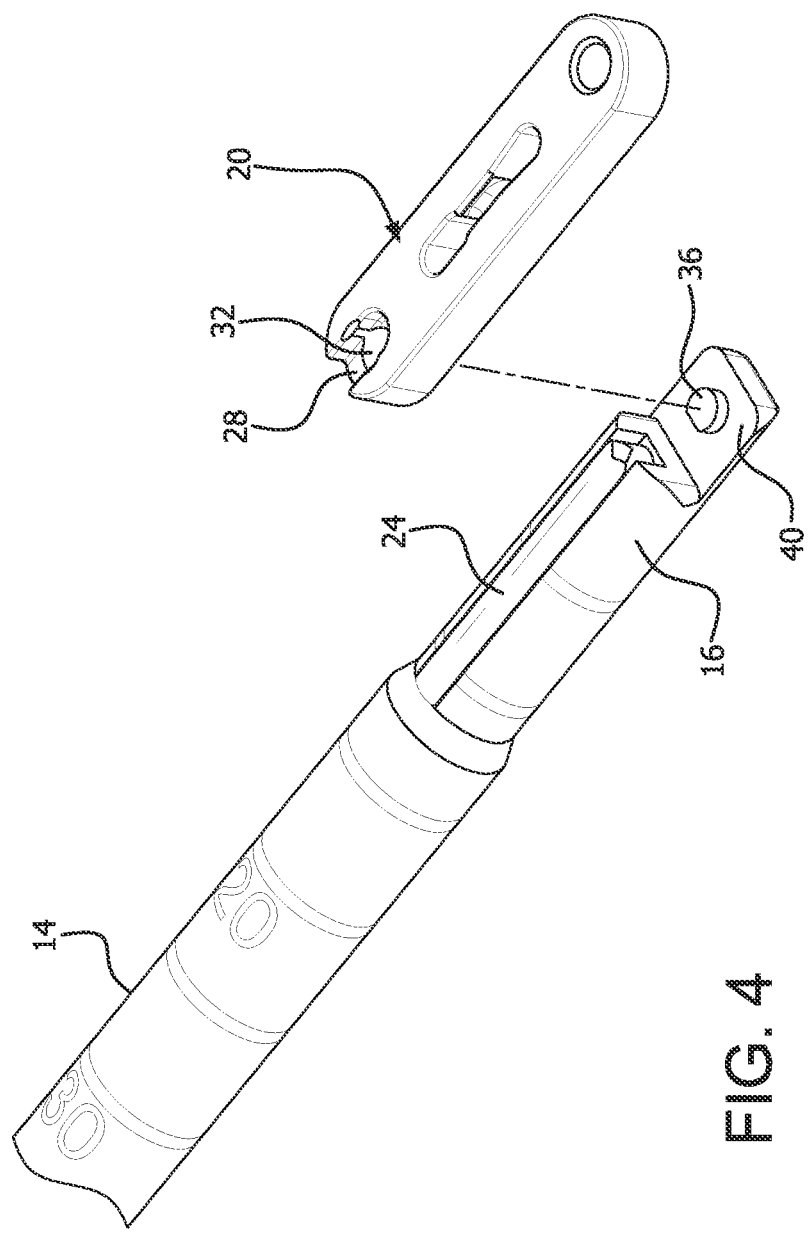
FIG. 4 is an exploded perspective view of a button inserter head and surgical button in a fully released position.

The surgical button 20 is secured between two projections of the button inserter head 16. One of these projections, in the form of tongue 24, is axially slidable relative to the axis of the elongated inserter shaft 14. As shown in FIG. 3, upon axial movement of the tongue 24 the distal end of the tongue 24 moves out of a cooperating groove 28 that is formed in the surgical button 20. As shown in FIG. 4, additional structure for securing the surgical button 20 in position on the inserter head 16 can be provided. In the embodiment shown, a radially inward extending protrusion in the form of pin 36 can be provided on projection 40 that is spaced from the opposing projection in the form of axially slidable tongue 24. The surgical button 20 has a depression such as the aperture 32 shown, which cooperates with the pin 36 two and additionally secures the surgical button 20 against axial and lateral movement.

Figure 5:
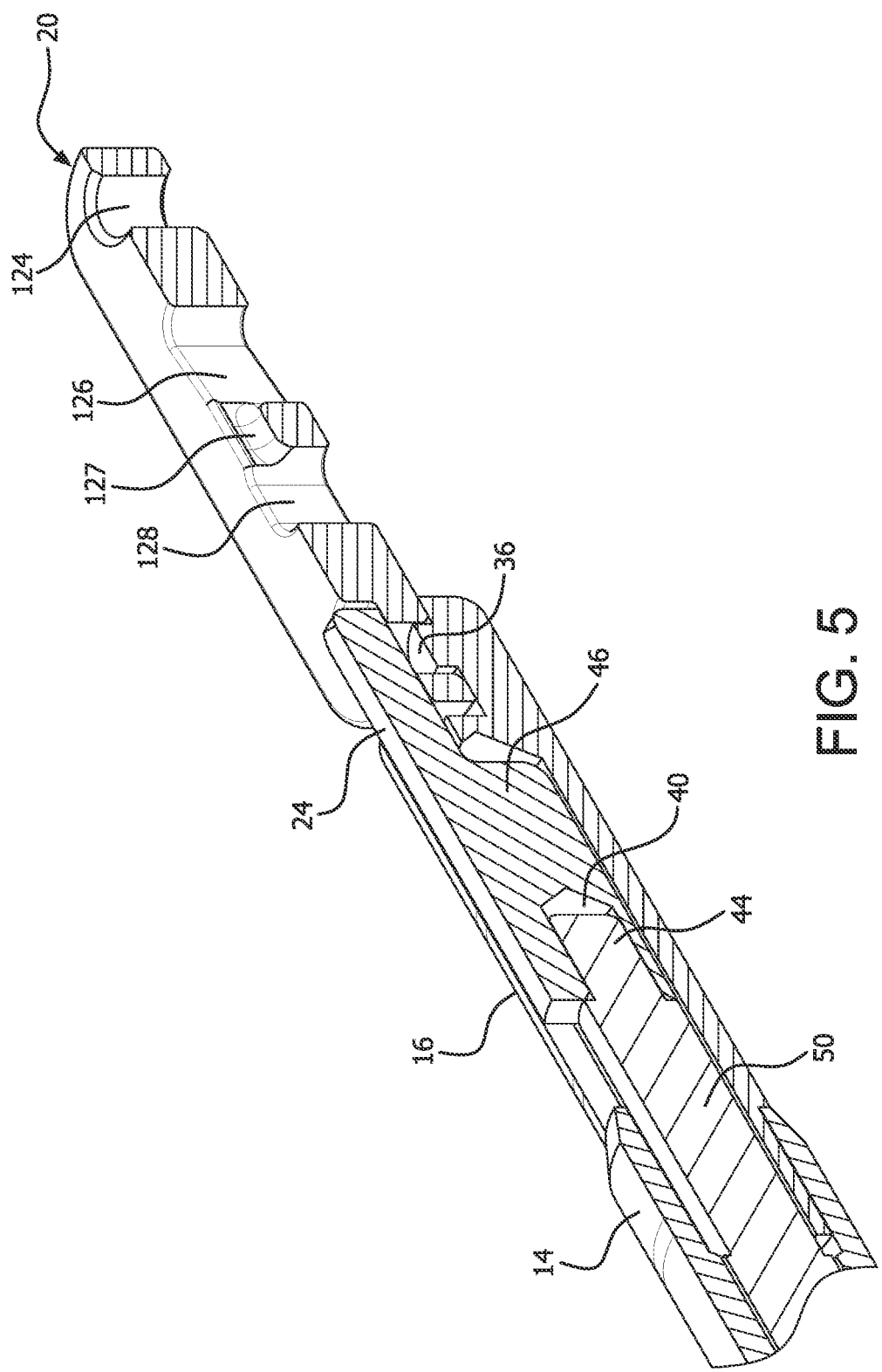
FIG. 5 is a cross section of a button inserter head and surgical button in a secured position.
Figure 6:
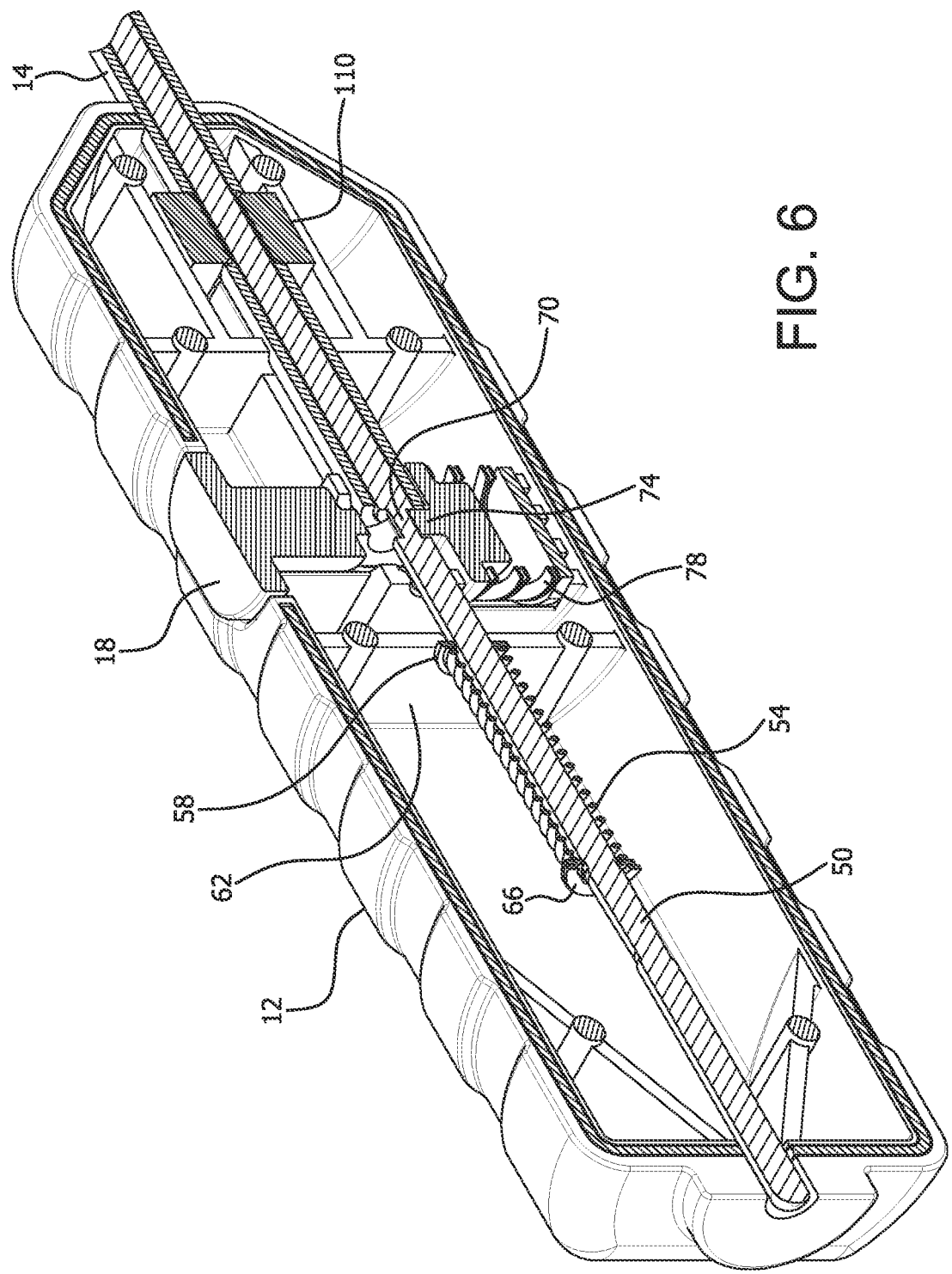
FIG. 6 is a rear perspective in cross-section of a button inserter handle in a secured position.
Figure 7:
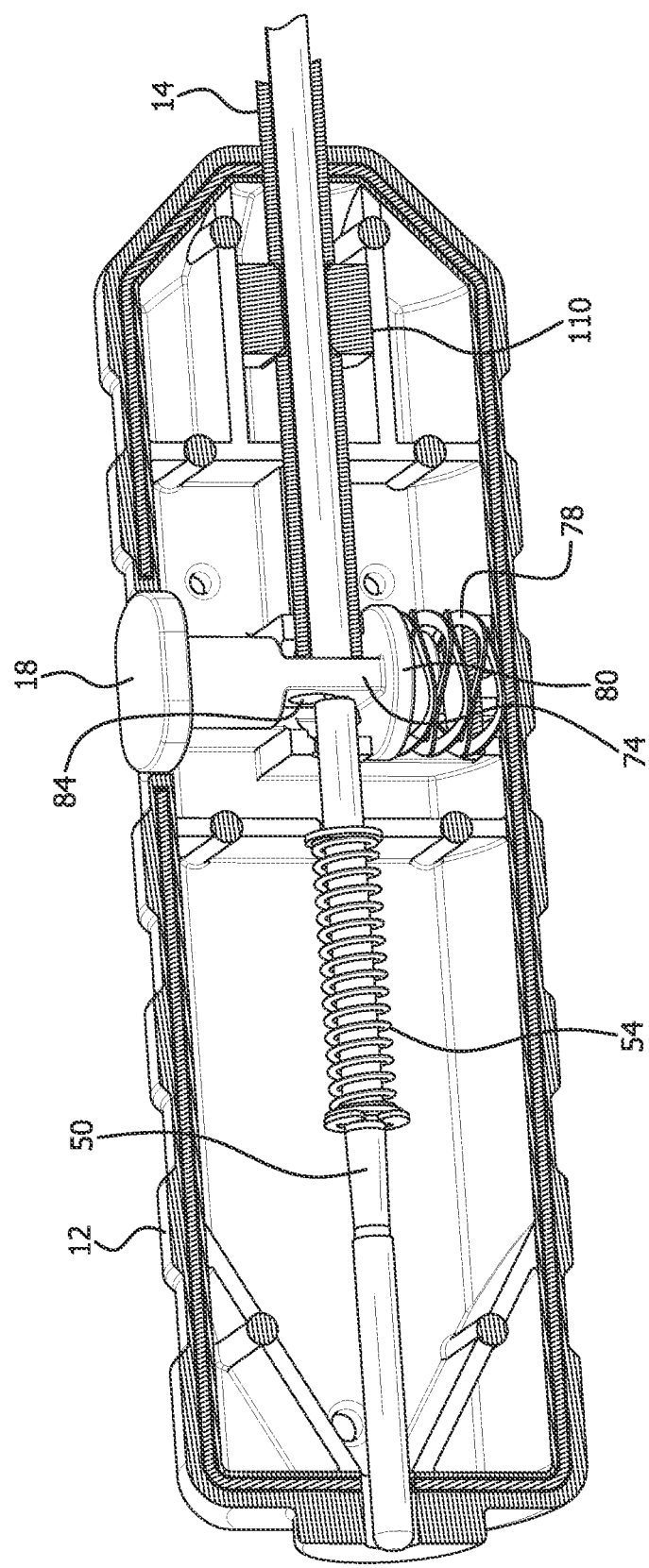
FIG. 7 is a side elevation in cross-section of a button inserter handle in a secured position.

The manner in which the surgical button 20 is released from the button inserter head 16 can vary. Mechanical actuators such as that shown, can vary in design. Electrical actuators such as solenoids are also possible. One embodiment is shown in the figures, and as shown in FIG. 5 the tongue can be supported by base 46 and axially slidable within the inserter head 16. An actuator shaft or release member 50 is axially movable within a tubular elongated inserter shaft 14. An opening 40 in the base 46 can receive distal end 44 of the release member 50, such that axial movement of the release member 50 will axially move the tongue 24 proximally and distally. The inserter shaft 14 can be tubular with an open interior to receive the release member actuator shaft 50.

The actuator assembly corresponding to the secured position of the surgical button 20 is shown in FIGS. 6-9. The release member actuator shaft 50 extends into the handle 12. An actuator shaft spring 54 is provided to bias the release member actuator shaft 50 for proximal movement. The actuator spring 54 can be secured at a spring seat 58 provided on wall 62 of handle 12, and to spring seat 66 secured to the release member actuator shaft 50.

Figure 8:
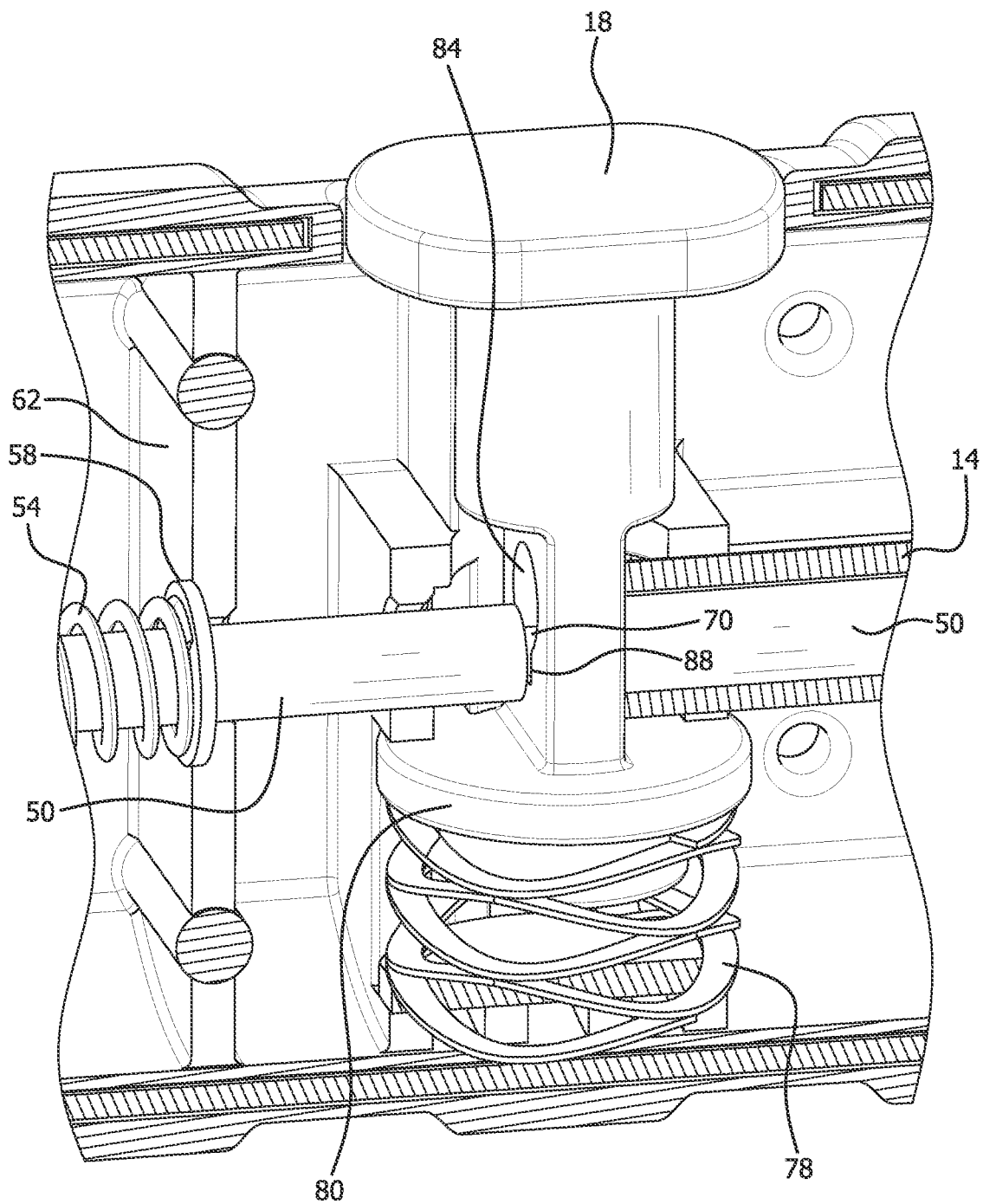
FIG. 8 is an enlarged perspective view, partially in cross-section, of a secure and release actuator assembly in a secured position.
Figure 9:
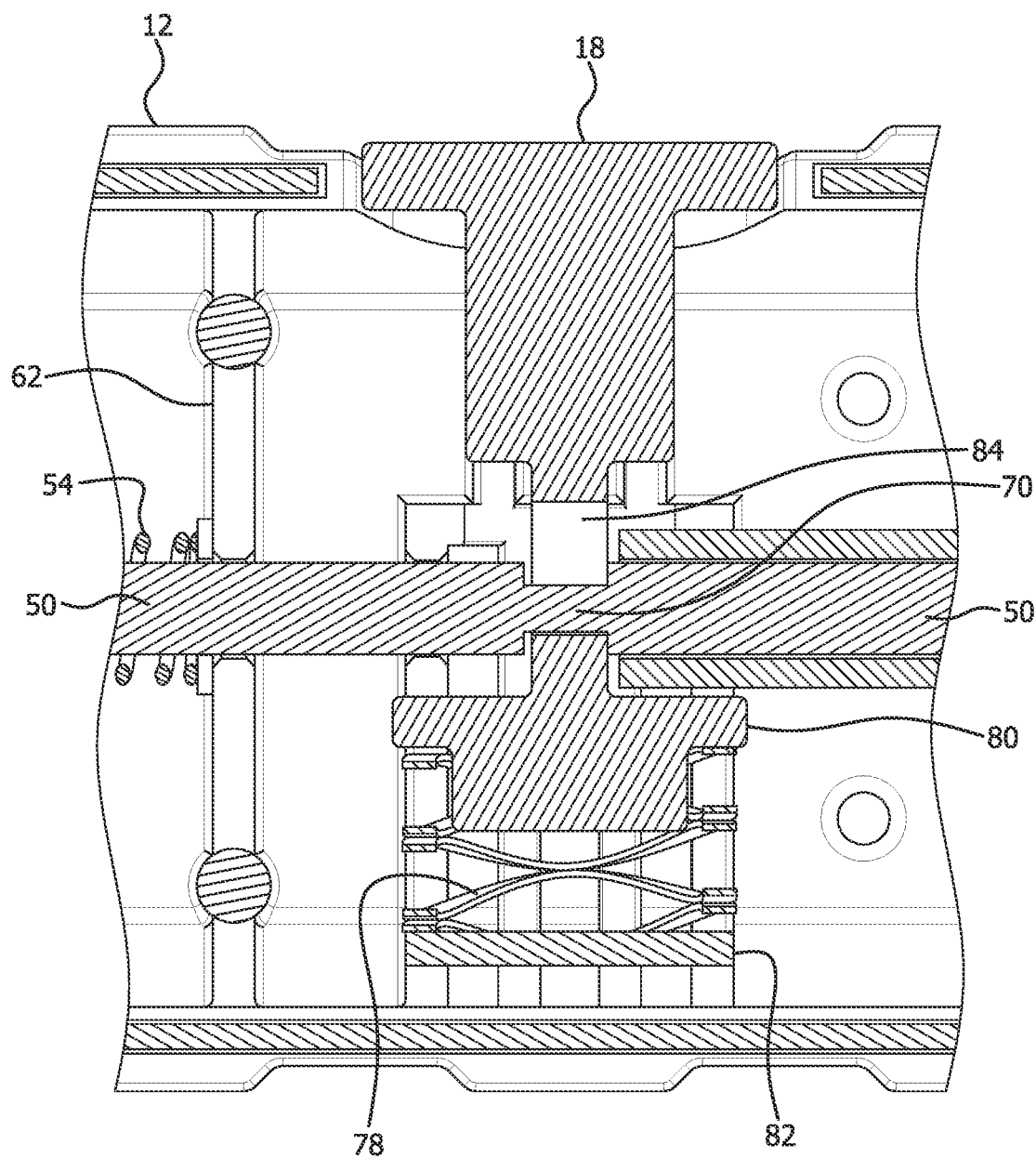
FIG. 9 is a side elevation in cross-section of a secure and release actuator assembly in a secured position.

The manner in which the release member actuator shaft 50 is secured and operated on the actuator assembly can vary. In the embodiment shown, the release member actuator shaft 50 has a narrowed neck portion 70. The actuator button 18 has a key portion 74. The actuator button 18 is biased by suitable structure such as actuator assembly spring 78, which can be provided between a spring seat 80 on the actuator button 18 and a spring seat 82 formed in the handle 12. The key opening of the key portion 74 includes a large opening 84 adapted to receive the full diameter of the release member actuator shaft 50, and a narrow neck opening portion 88 which is dimensioned to receive the narrowed neck 70 but not the full diameter of the release member actuator shaft 50. In the secured position, as shown in FIGS. 8-9, the narrowed neck 70 is secured within the narrowed neck opening 88 of the key portion 74 by the biasing action of actuator assembly spring 78. The elongated shaft 14 and release member actuator shaft 50 can be supported by suitable structure such as bushing 110.

Figure 10:
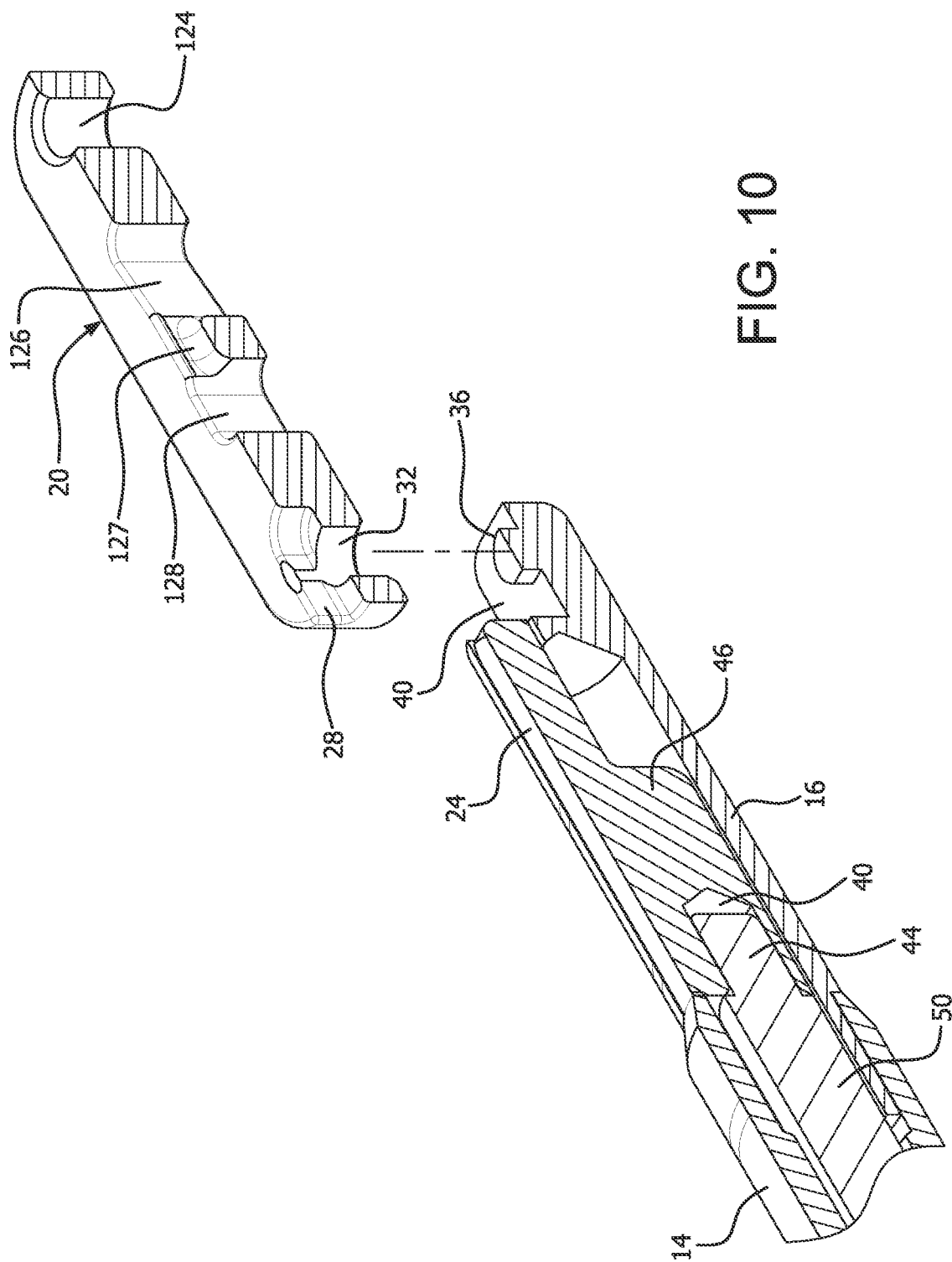
FIG. 10 is a perspective view in cross-section of a button inserter head and button in a released position.
Figure 11:
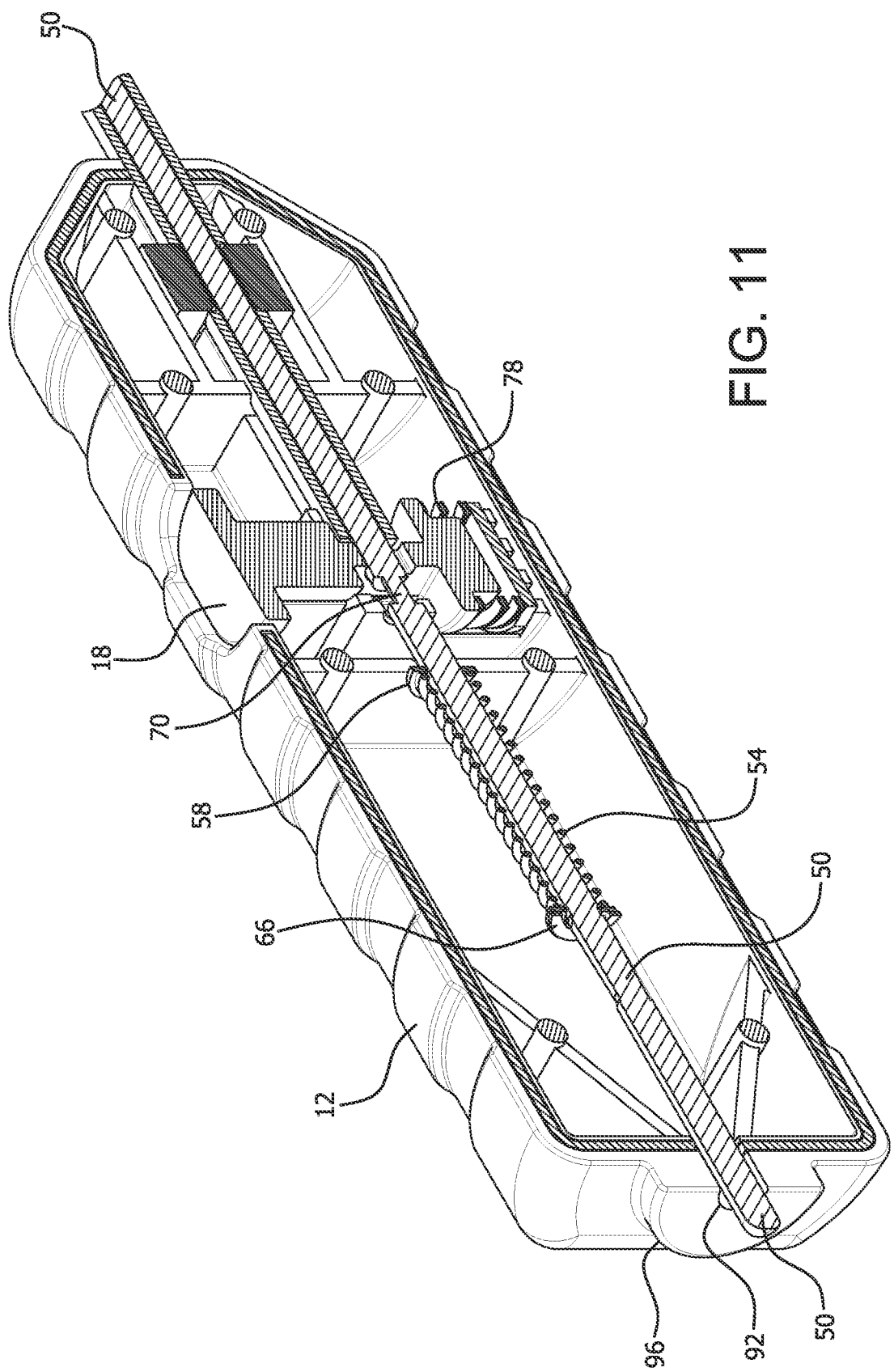
FIG. 11 is a rear perspective view in cross-section of a button inserter handle in a released position.
Figure 12:
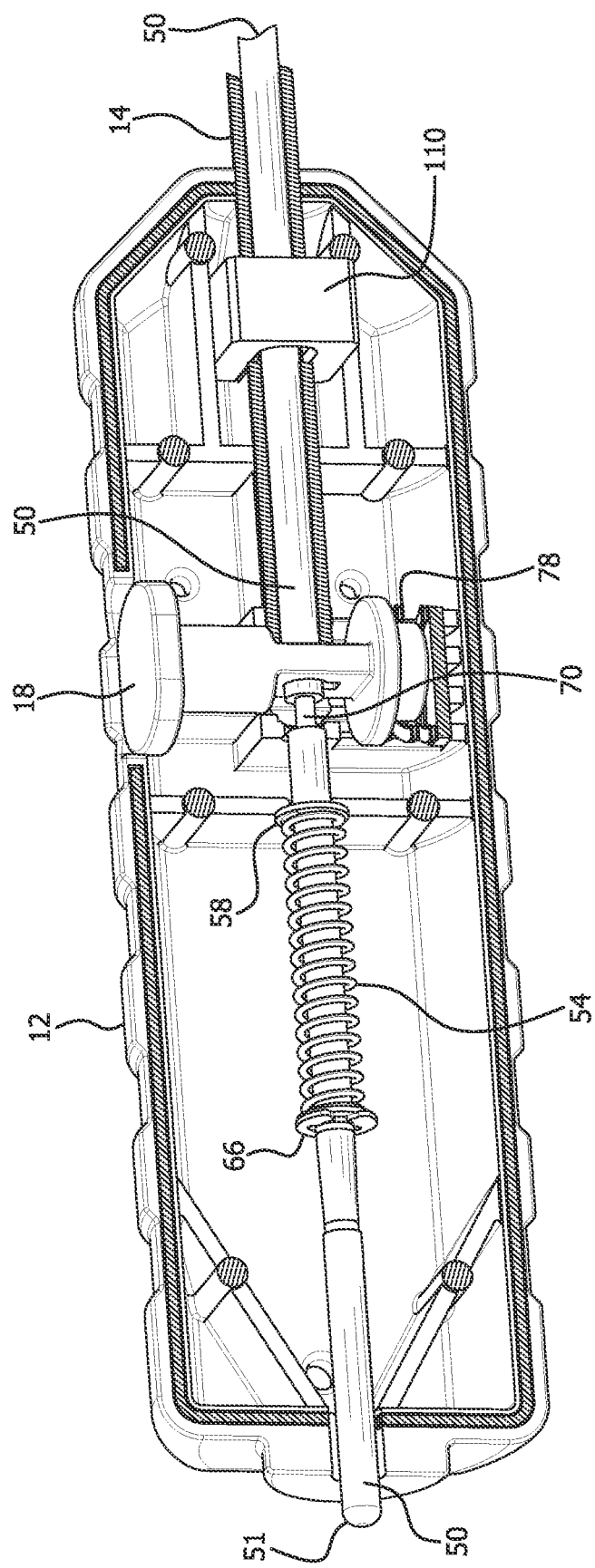
FIG. 12 is a side elevation in cross section of a button inserter handle in a released position.
Figure 13:
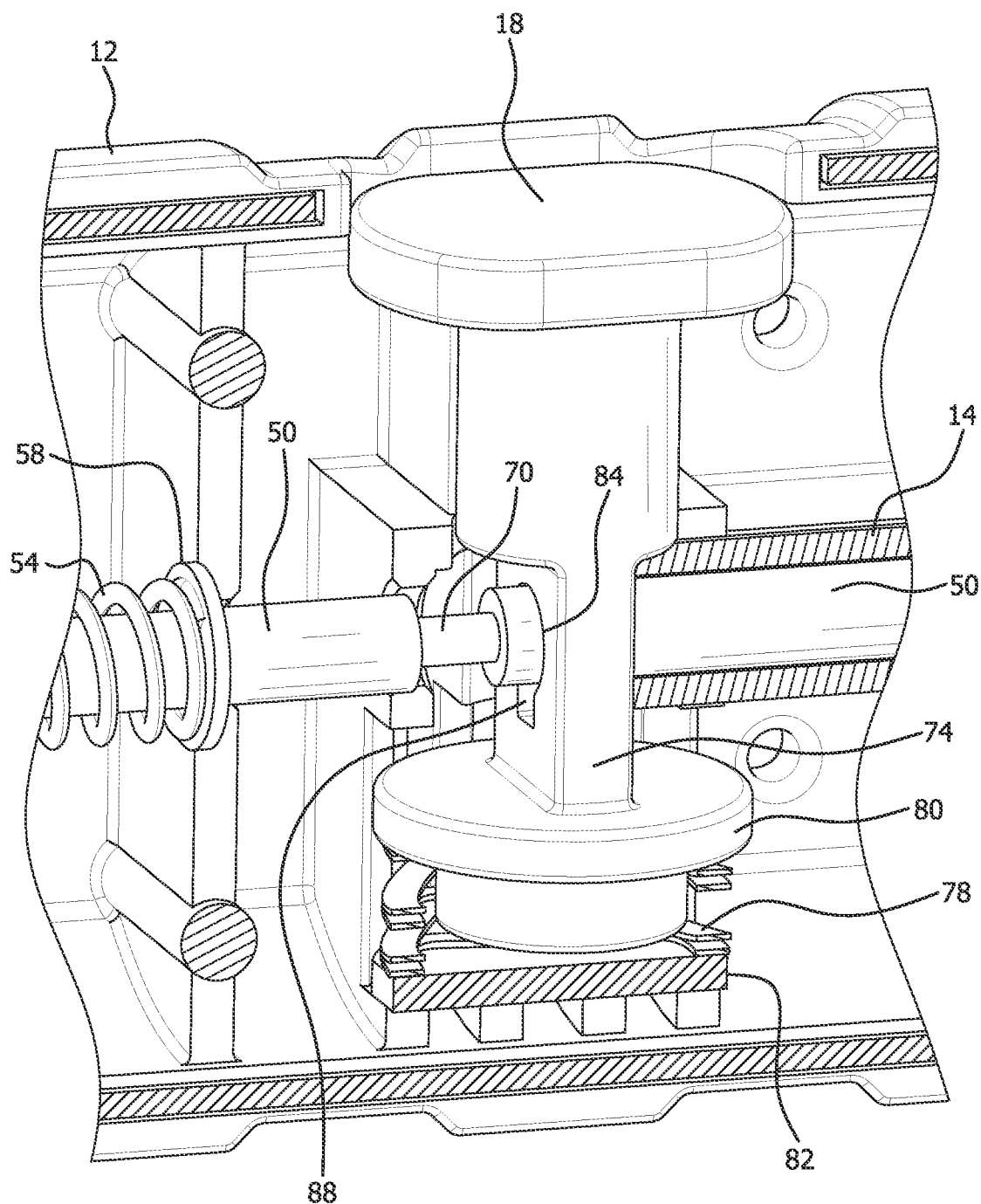
FIG. 13 is an enlarged perspective view, partially in cross-section, of a secure and release actuator assembly in a released position.
Figure 14:
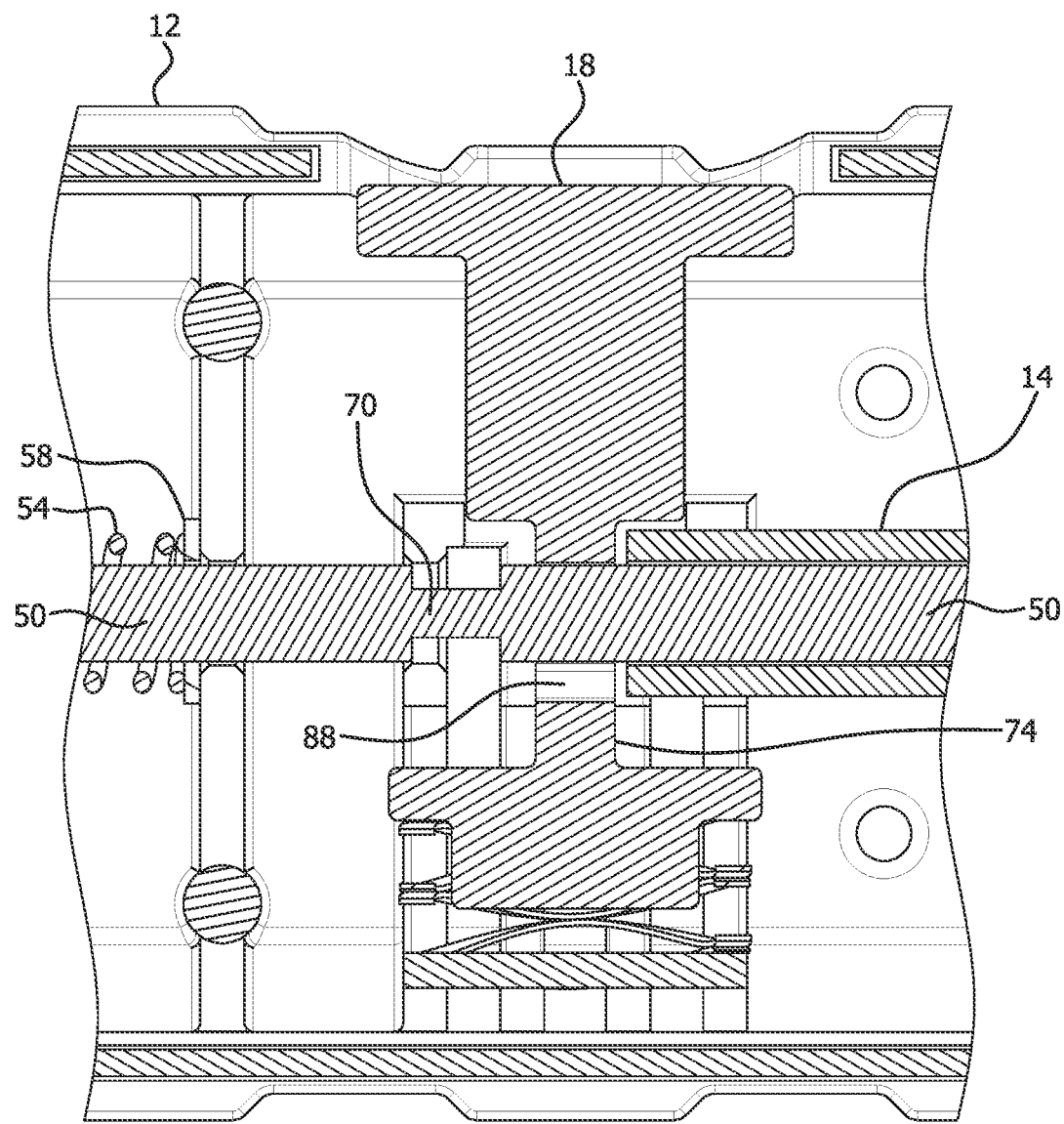
FIG. 14 is a side elevation in cross-section of a secure and release actuator assembly in a released position.

Release of the surgical button 20 from the button inserter 10 is shown in FIGS. 10-14. Depression of the actuator button 18 against the biasing of actuator assembly spring 78 moves the key portion 74 such that the large opening 84 is aligned with the release member actuator shaft 50. As the large opening 84 is dimensioned to permit passage of the actuator shaft 50, the actuator shaft 50 will be urged by the actuator shaft spring 54 proximally and through the large opening 84. An opening 92 can be provided in rear portion 96 of the handle 12 to permit proximal end 51 of the release member actuator shaft 50 to move proximally. The narrowed neck portion 70 will also move proximally, as shown particularly in FIGS. 12-14. As shown in FIG. 10, the tongue 24 will move proximally with the actuator shaft 50 to permit release of the surgical button 20.

Figure 15:
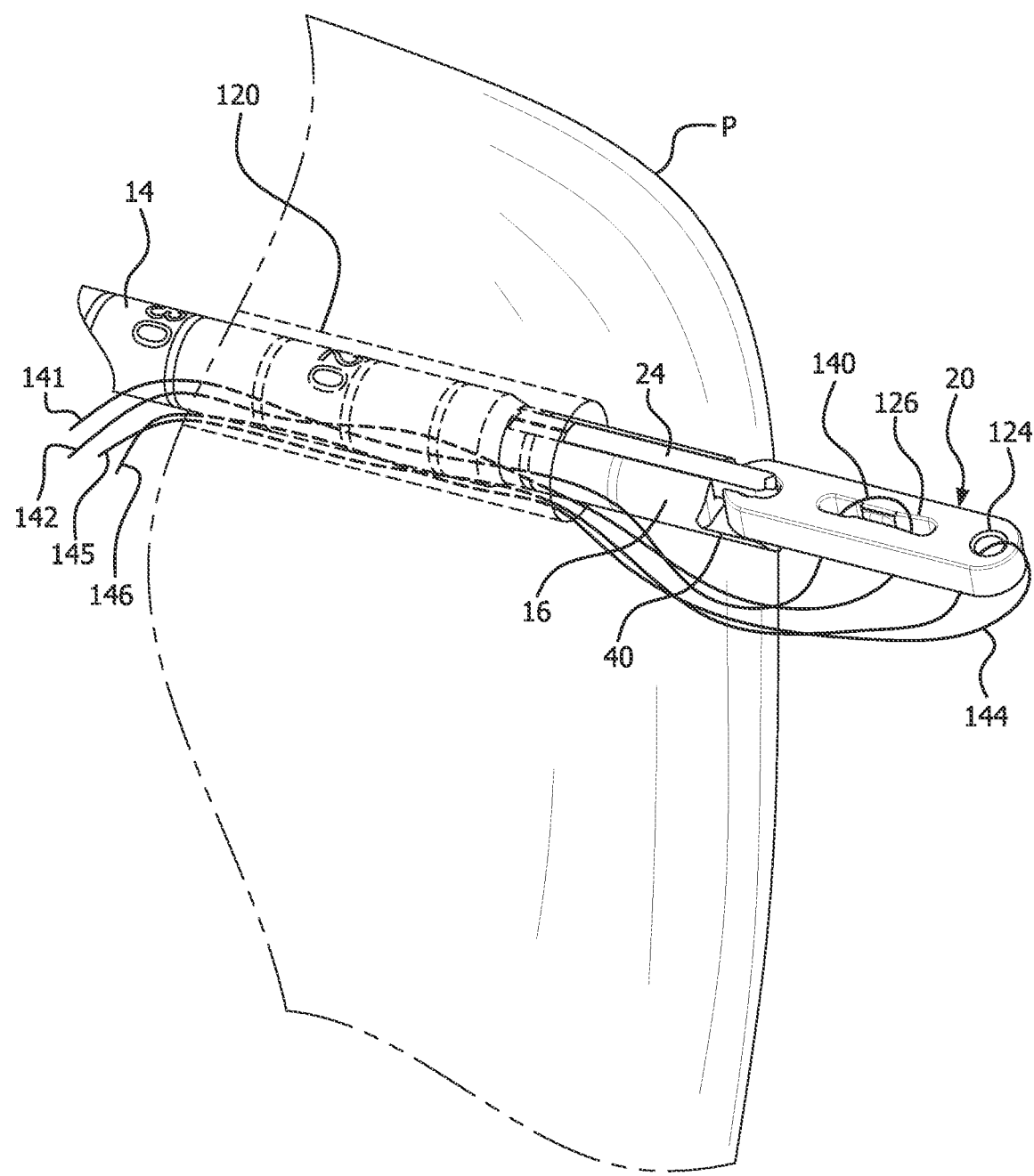
FIG. 15 is a perspective view, partially in phantom, of a button inserter head and surgical button in a first mode of a button insertion surgical procedure.
Figure 16:
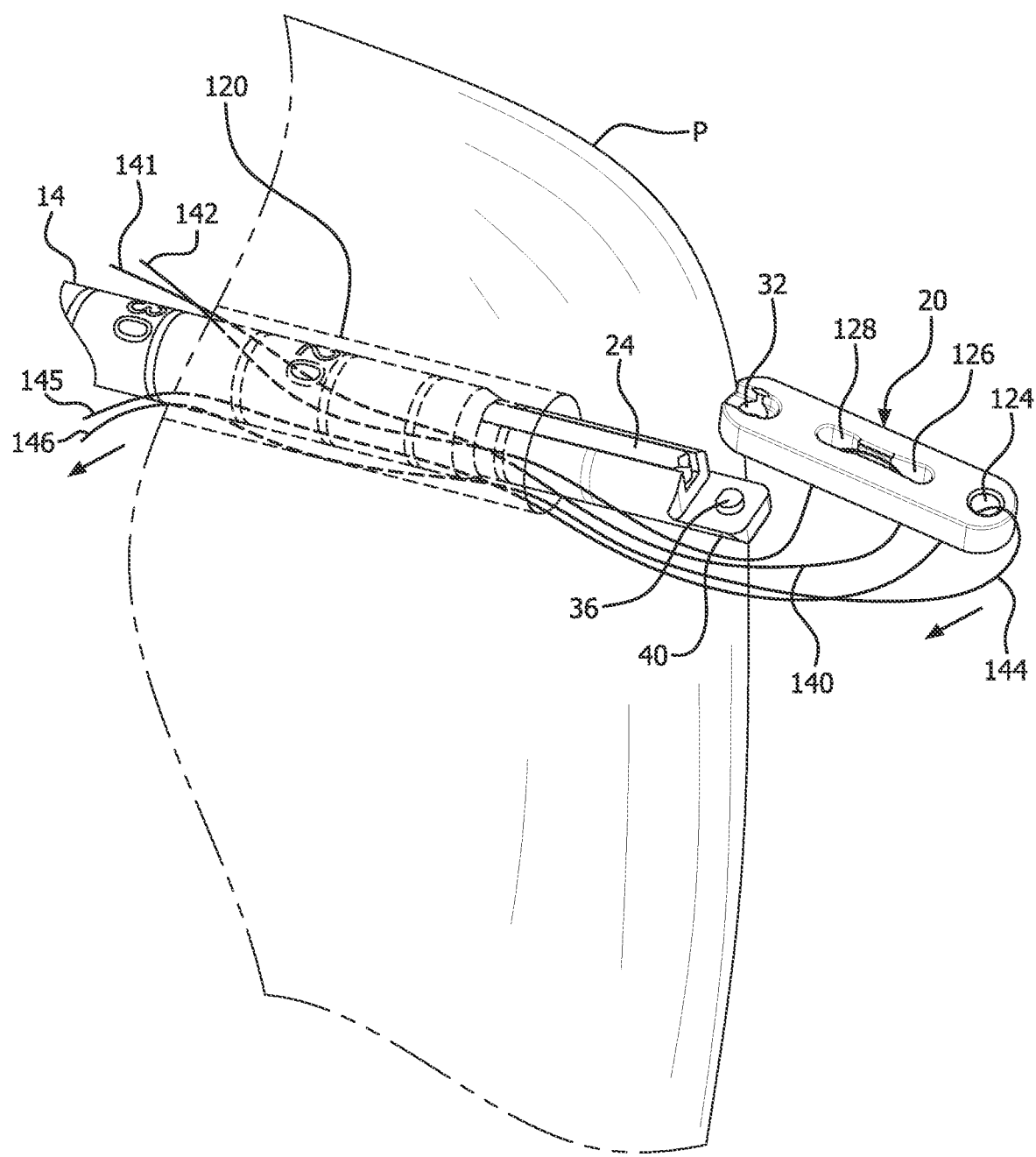
FIG. 16 is a perspective view, partially in phantom, of a button inserter head and surgical button in a second mode of a button insertion surgical procedure.
Figure 17:
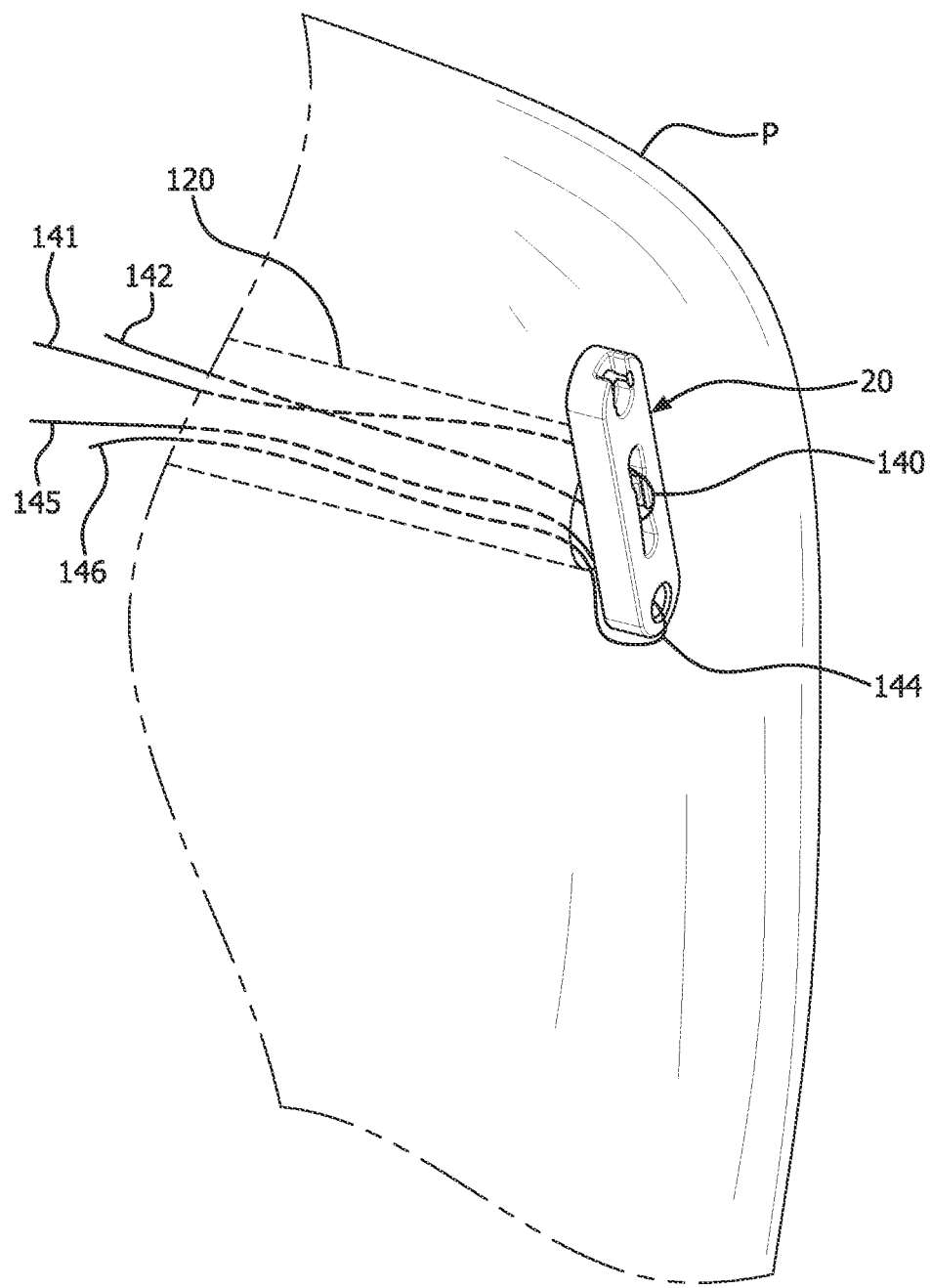
FIG. 17 is a perspective view, partially in phantom, of a surgical button in a third mode of a button insertion surgical procedure.
Figure 18B:
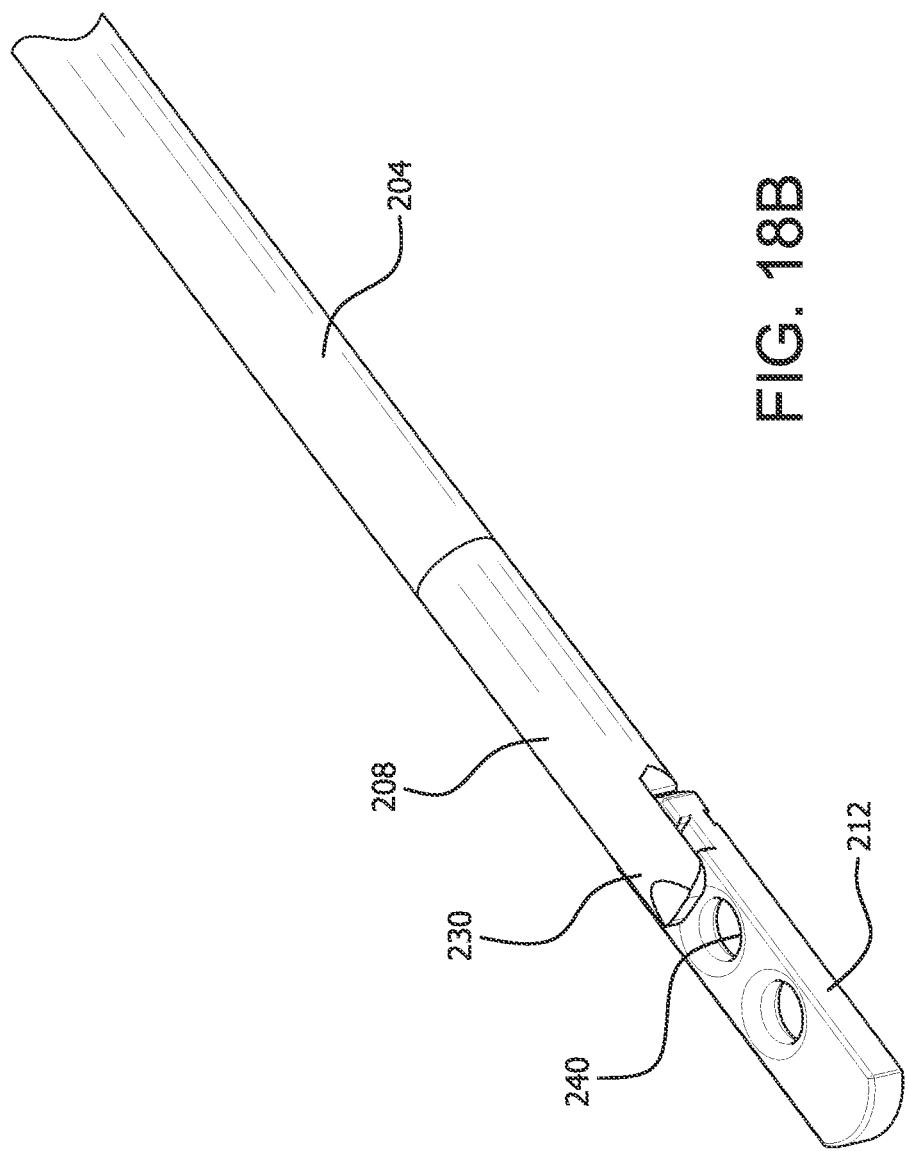
FIG. 18B is a magnified view of an alternative inserter head.
Figure 19B:
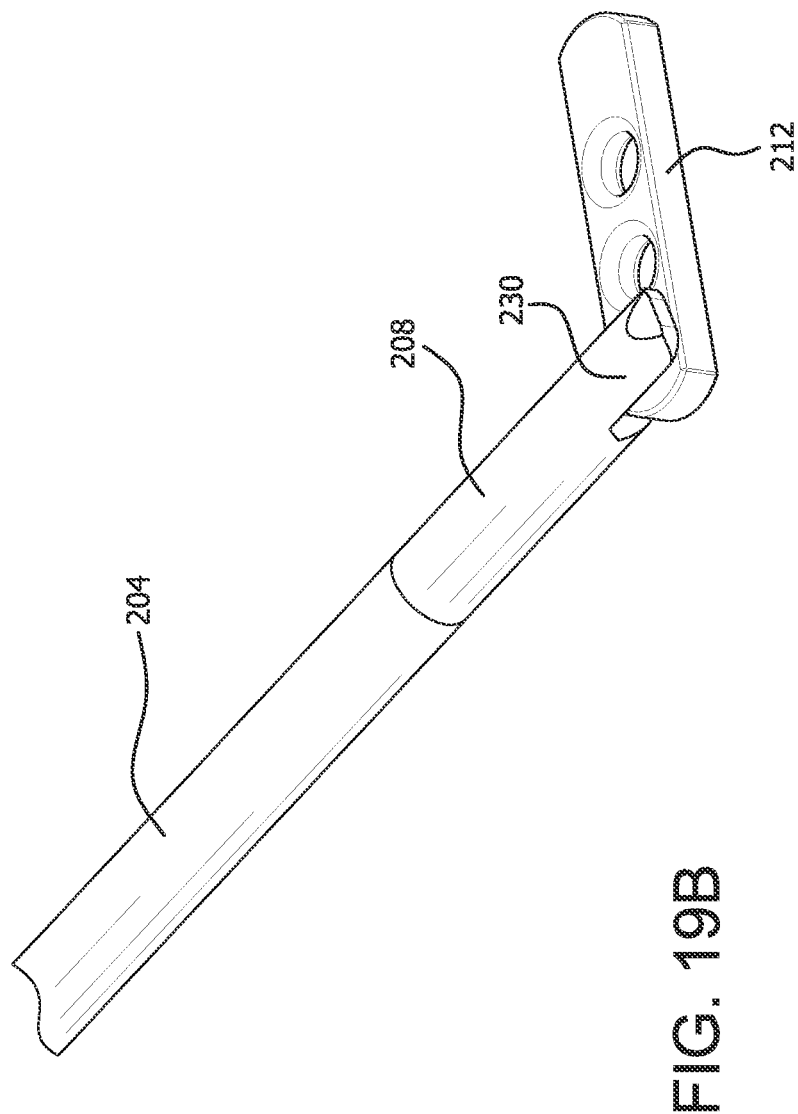
FIG. 19B is a magnified view of the alternative inserter head in the second mode of operation.

Operation of the device is shown in FIGS. 15-17. The inserter head is inserted through a tunnel 120 formed in a bony portion of the patient P. Suture 140 is looped through openings 126 and 128 of surgical button 20. Ends 141 and 142 of suture 140 extend through the tunnel 120. A manipulation suture 144 is threaded through opening 124 at the distal end of surgical button 20, and ends 145-146 of manipulation suture 144 extend through the tunnel 120. The surgical button 20 is held securely in position between tongue 24 and projection 40. The inserter head 16 is extended into the tunnel 120 until the surgical button 20 emerges from the tunnel 120 as shown in FIG. 15.

Once the surgical button 120 is in the proper position, it is ready to be released. The actuator button 18 is depressed, causing proximal movement of the release member actuator shaft 50 and proximal movement of the tongue 24, as shown in FIG. 16. The surgical button 20 will be positioned on the inserter head 16 with the pin 36 in the aperture 32. Operation of the manipulation suture 144 by a proximal movement of the ends 145-146 will cause pivoting movement of the distal end of the surgical button 20 about the distal end of the projection 40. This will remove the proximal end of the button 20 from the pin 36 and projection 40. Further manipulation of the surgical button 20 by movement of the ends 145-146 of the manipulation suture 144, as well as ends 141-142 of the suture 140, will place the surgical button in the resting position spanning the tunnel 120 and abutting the bone of patient P, as shown in FIG. 17.

There is shown in FIGS. 18-27 an alternative embodiment of a button inserter assembly, which utilizes an alternative button inserter apparatus 200 and an alternative surgical button 212. The button inserter apparatus 200 includes an elongated inserter shaft 204, an alternative inserter head 208, and an inserter actuator shaft 216. The inserter head 208 has an axially movable engagement projection 220 having a radially inwardly extending cam protrusion 222 and is slidable in a groove 224 formed in the inserter head 208 (FIG. 20B). A fixed or immovable engagement projection 230 has a radially inwardly extending engagement protrusion 234. As shown also in FIGS. 24-25, the axially movable engagement projection 220 can be fixed to a mounting barrel portion 221 for engagement to the actuator shaft 216 such that movement of the actuator shaft 216 will axially move the mounting barrel portion 221, engagement projection 220 and cam protrusion 222.

Figure 22:
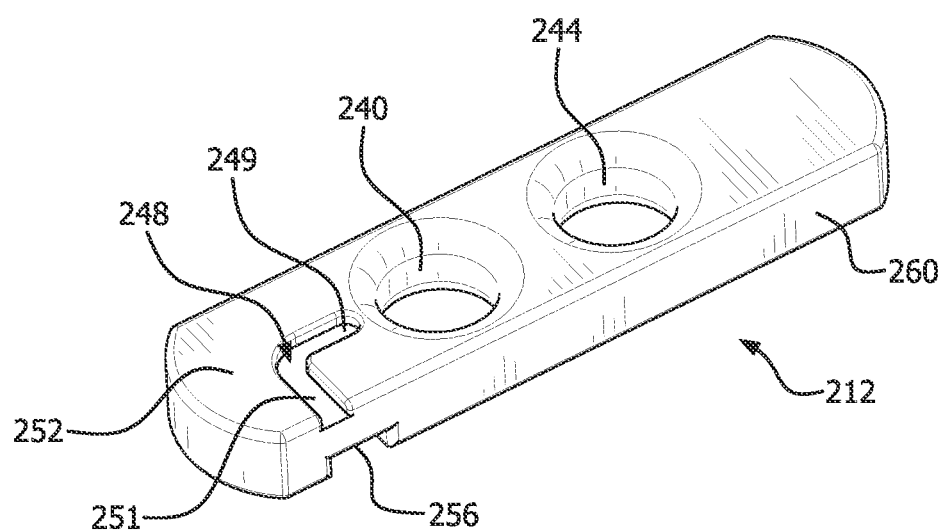
FIG. 22 is a top perspective view of a surgical button according to the alternative embodiment.
Figure 23:
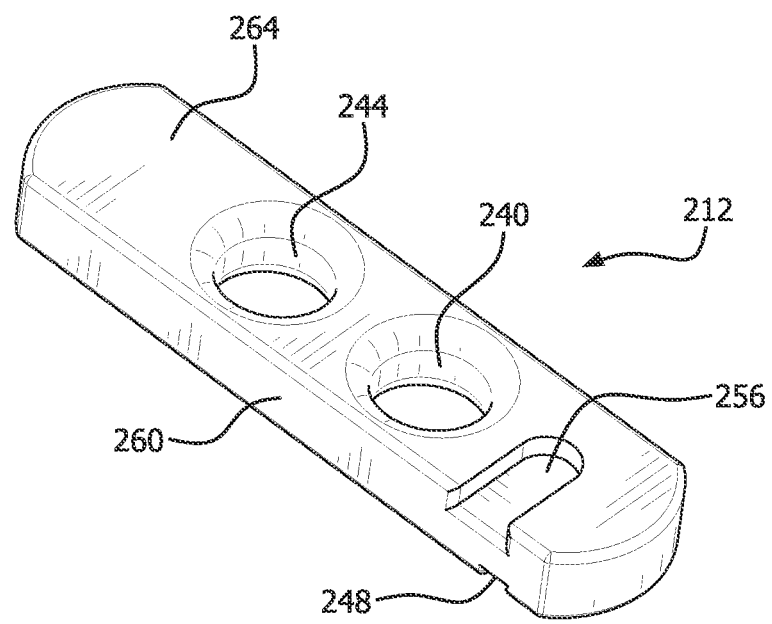
FIG. 23 is a bottom perspective view of the surgical button according to the alternative embodiment.
Figure 24:
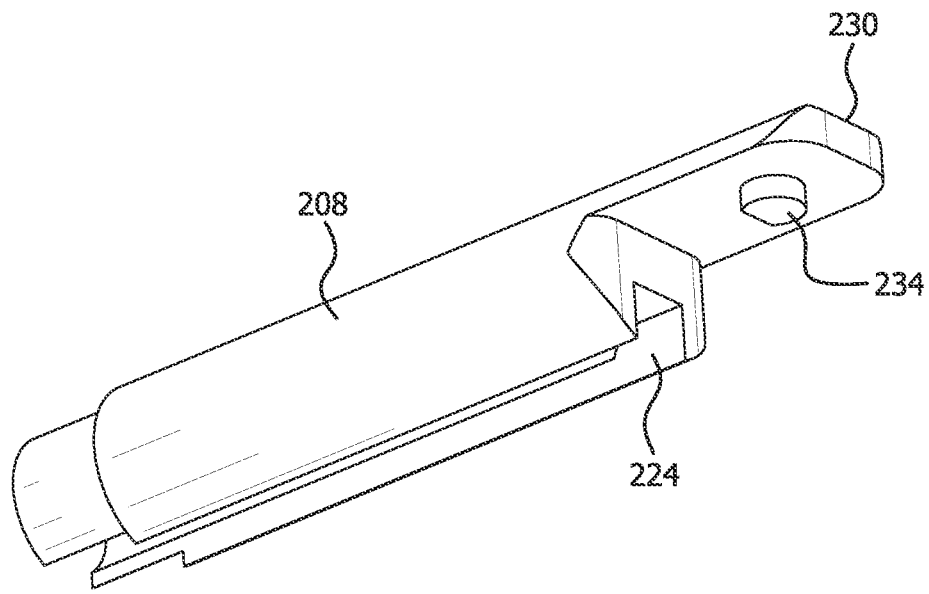
FIG. 24 is a bottom perspective view of an inserter head according to the alternative embodiment.
Figure 25:
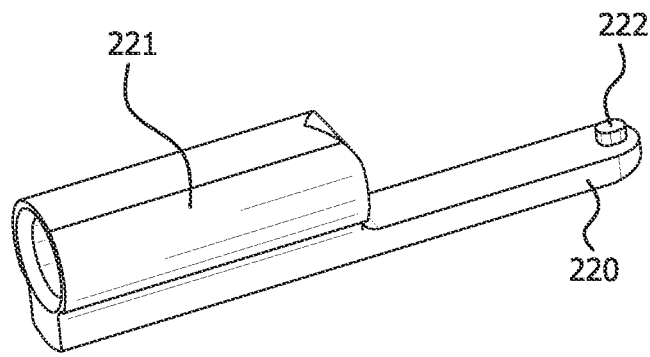
FIG. 25 is a bottom perspective view of an axially movable tongue.

The alternative surgical button 212 is shown particularly in FIGS. 22-23. The surgical button 212 has suture openings 240 and 244 as shown, but can have any size, shape or number of such openings or other structure suitable for surgical buttons. The surgical button 212 has a curved groove 248 which is comprised of a medial, axially extending portion 249 and a laterally extending portion 251 formed in an elongated first large face 252 of the surgical button 212 (FIG. 22). The laterally extending portion 251 extends to elongated side face 260 of the button 212 to permit the egress of the cam protrusion 222 as will be described. A second elongated large face 264 opposite to the first large face 252 has a transverse groove 256 extending from a medial position to the elongated side face 260 (FIG. 23). The transverse groove 256 engages the engagement protrusion 234.

Operation of the alternative embodiment is shown in FIGS. 26A-26E and FIGS. 27A-27E. In the initial position (FIG. 26A, FIG. 27A), the cam protrusion 222 is positioned in a medial, axially extending portion 249 of curved groove 248. The protrusion 234 is positioned in the transversely extending groove 256 in a medial portion of the surgical button 212. The surgical button 212 is securely engaged between the engagement projection 220 and the engagement projection 230.

Figure 26A:
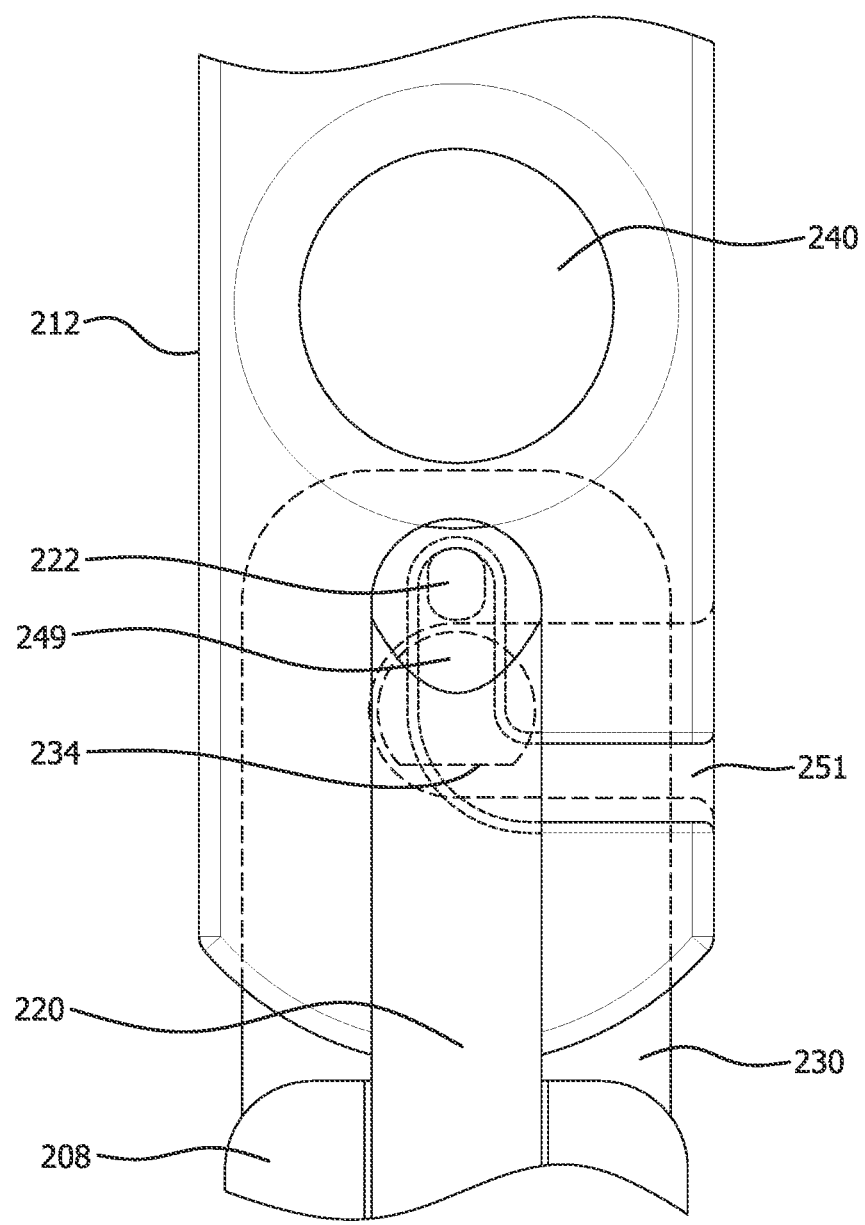
FIG. 26A is an enlarged plan view of an inserter head and surgical button according to the alternative embodiment, partially in phantom in a first mode of operation.
Figure 26B:
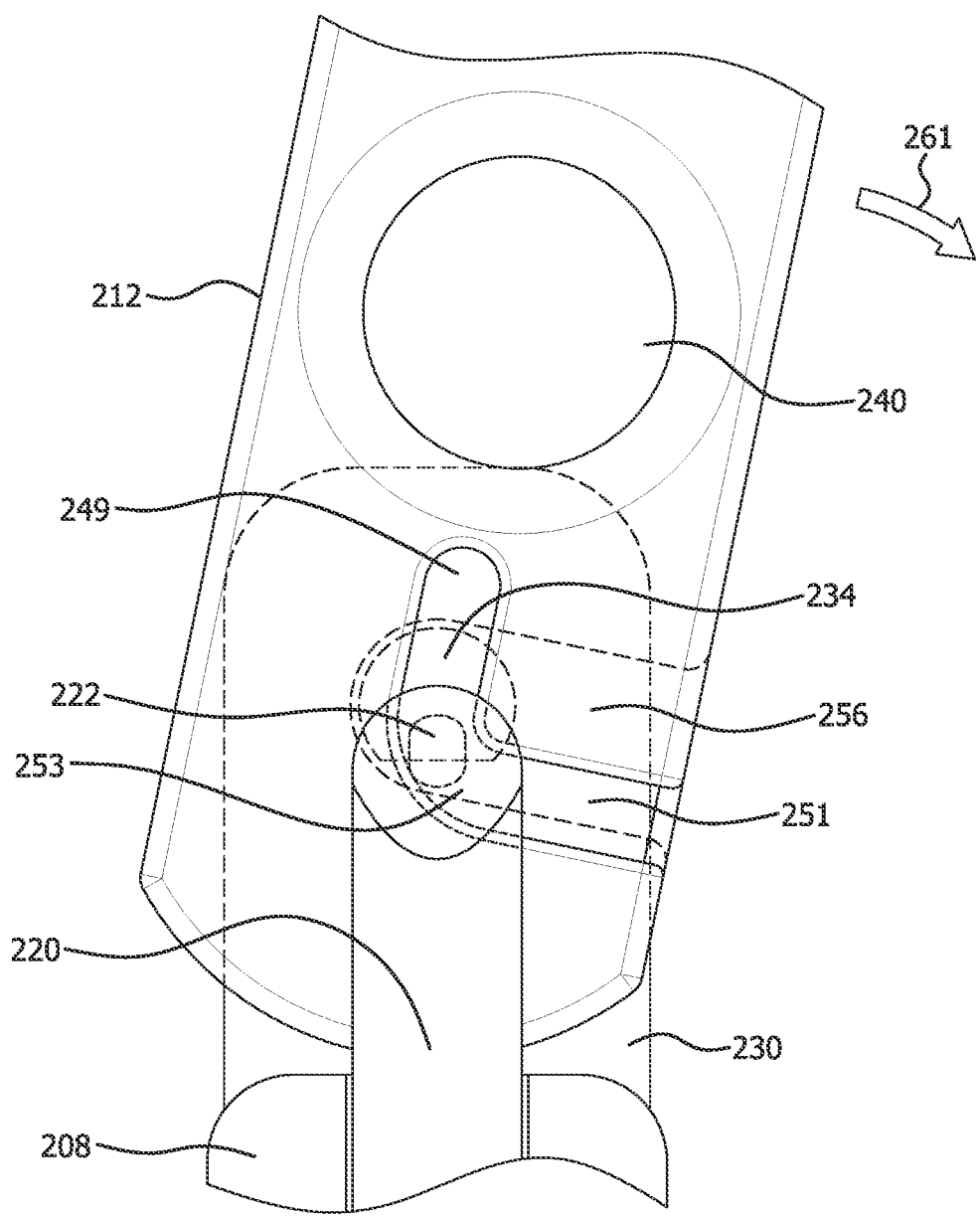
FIG. 26B is in second mode of operation.
Figure 26C:
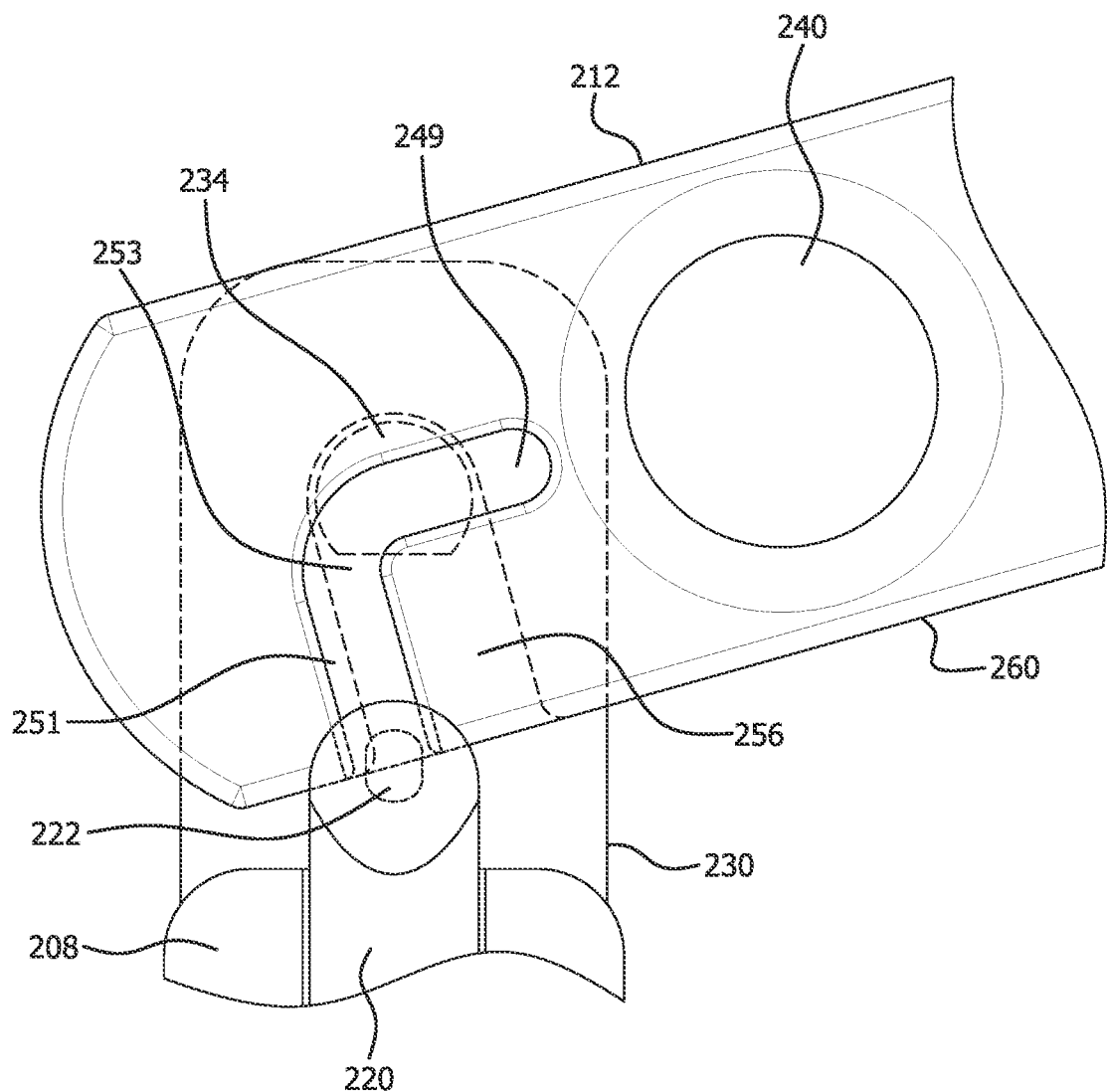
FIG. 26C is in a third mode of operation.
Figure 26D:
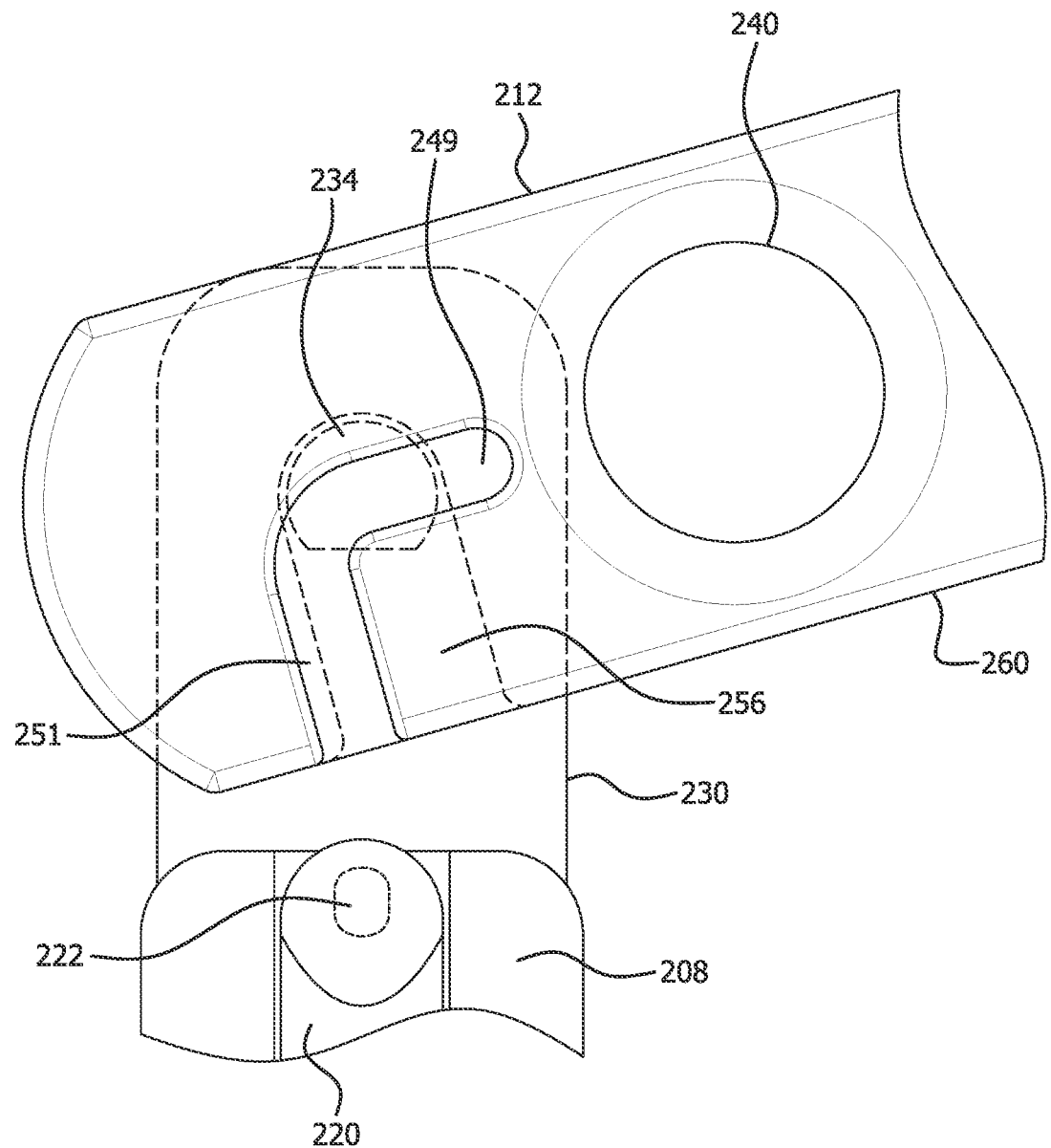
FIG. 26D is in a fourth mode of operation.
Figure 26E:
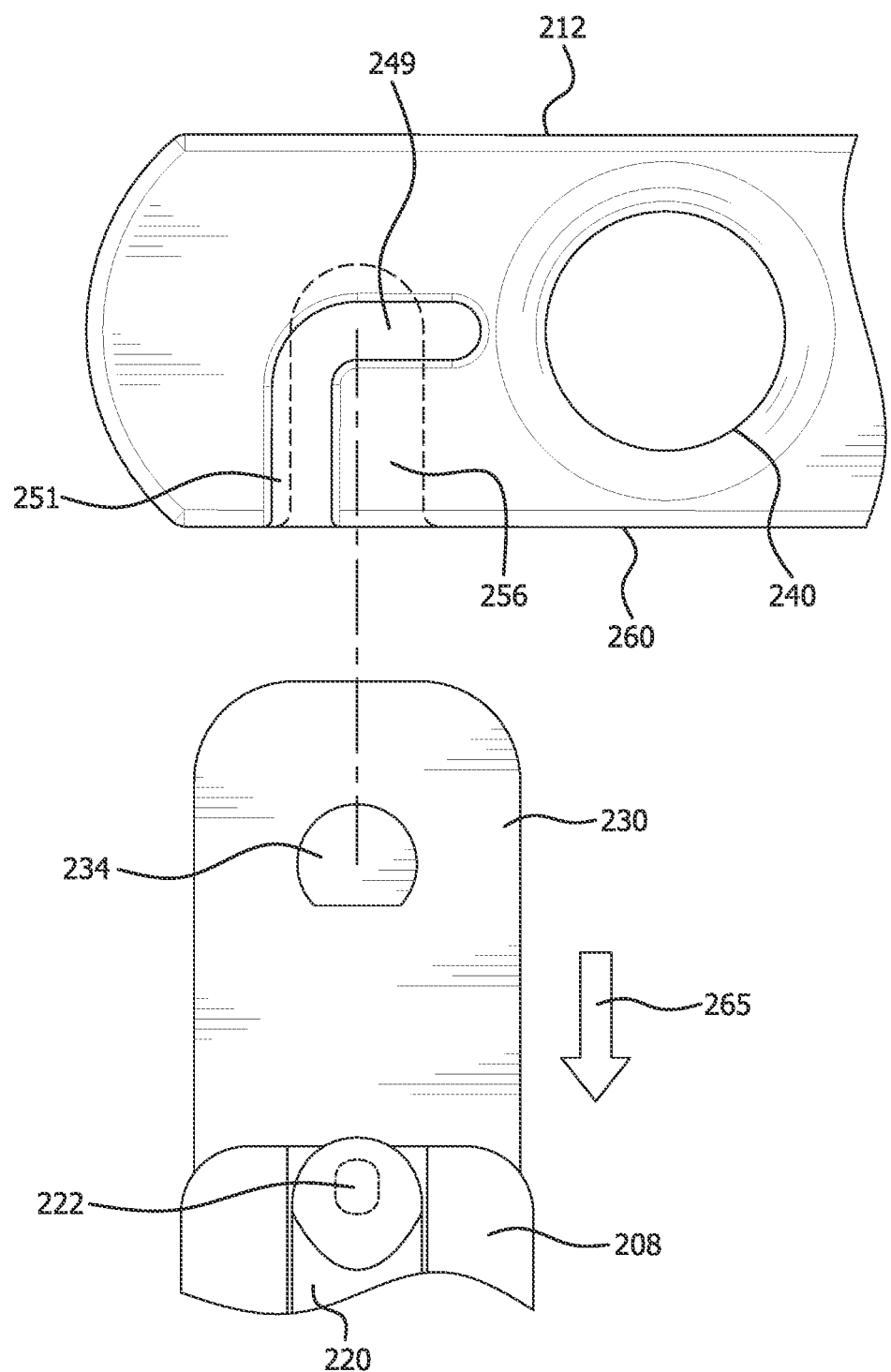
FIG. 26E is a fifth mode of operation.
Figure 27A:
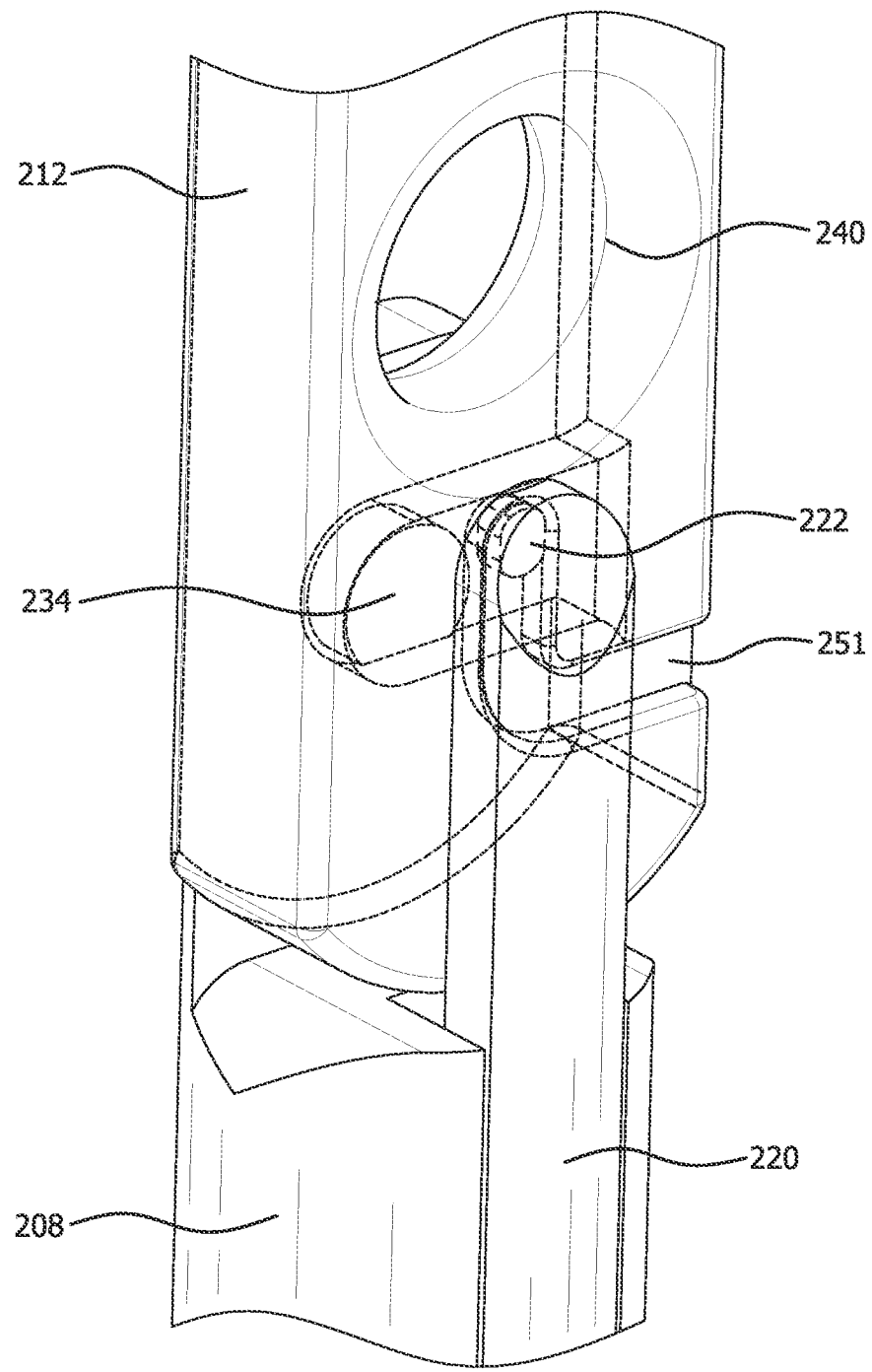
FIG. 27A is an enlarged plan view of an inserter head and surgical button according to the alternative embodiment of FIG. 26A, partially in phantom and in the first mode of operation.
Figure 27B:
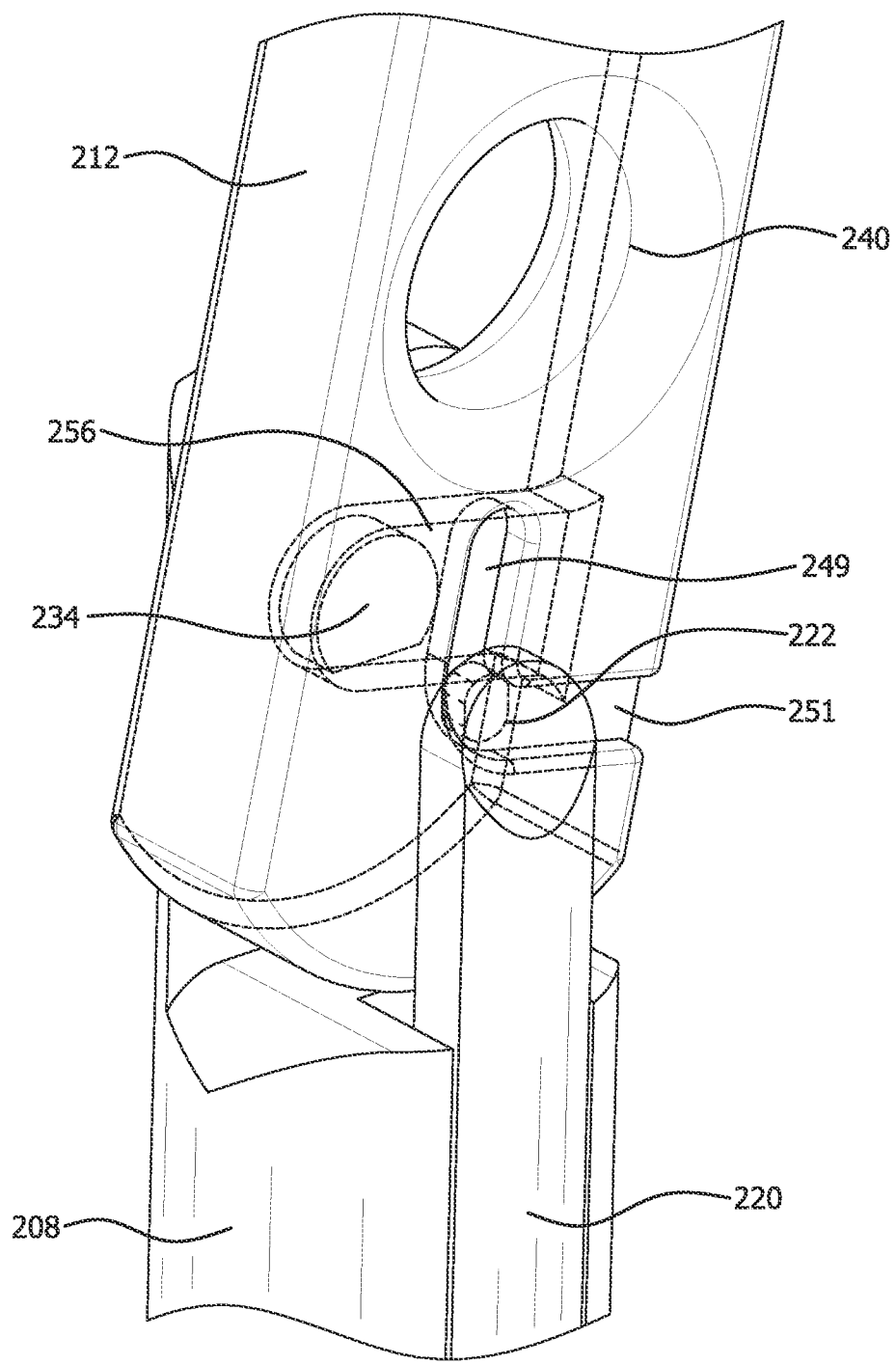
FIG. 27B is in the second mode of operation.
Figure 27C:
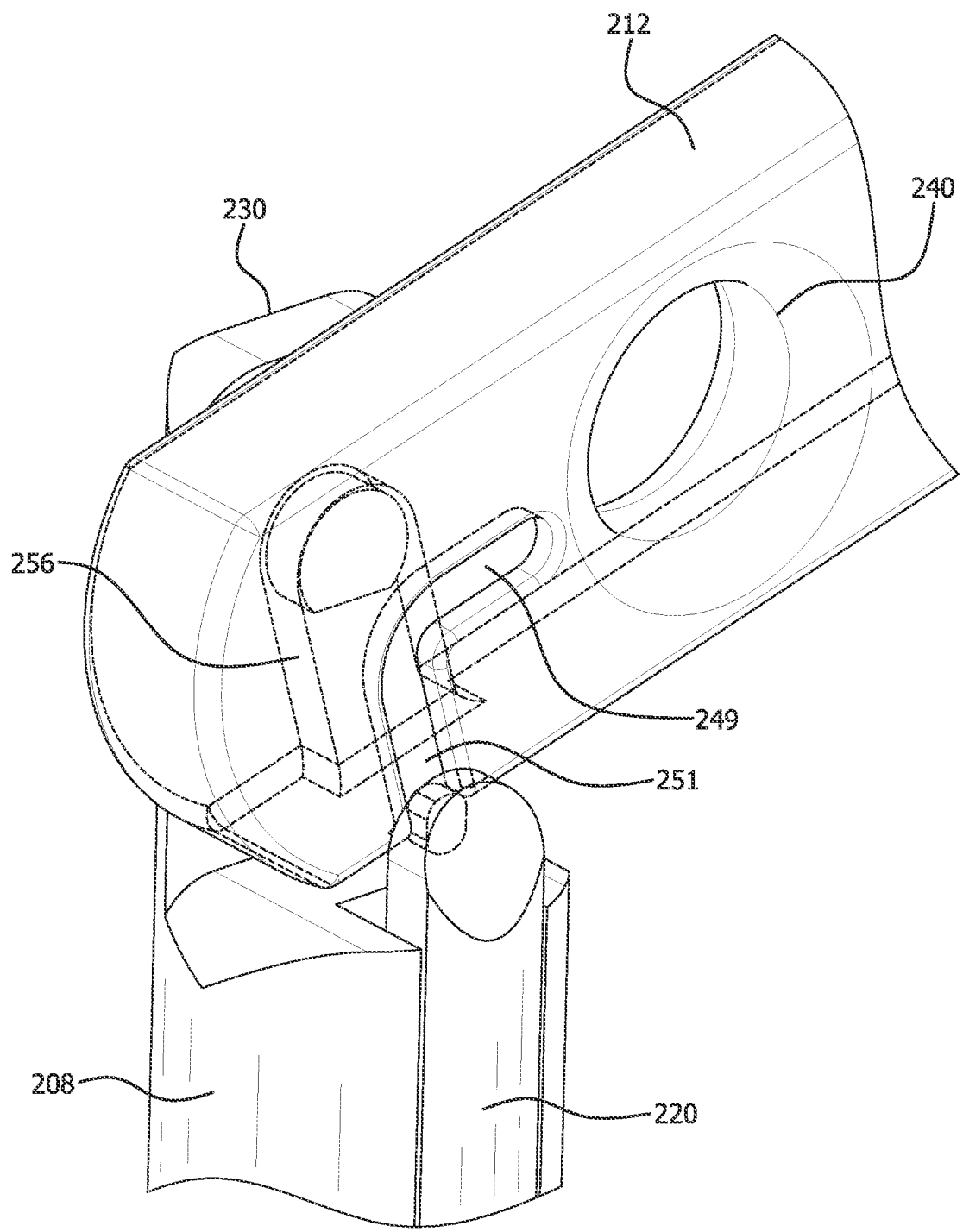
FIG. 27C is in the third mode of operation.
Figure 27D:
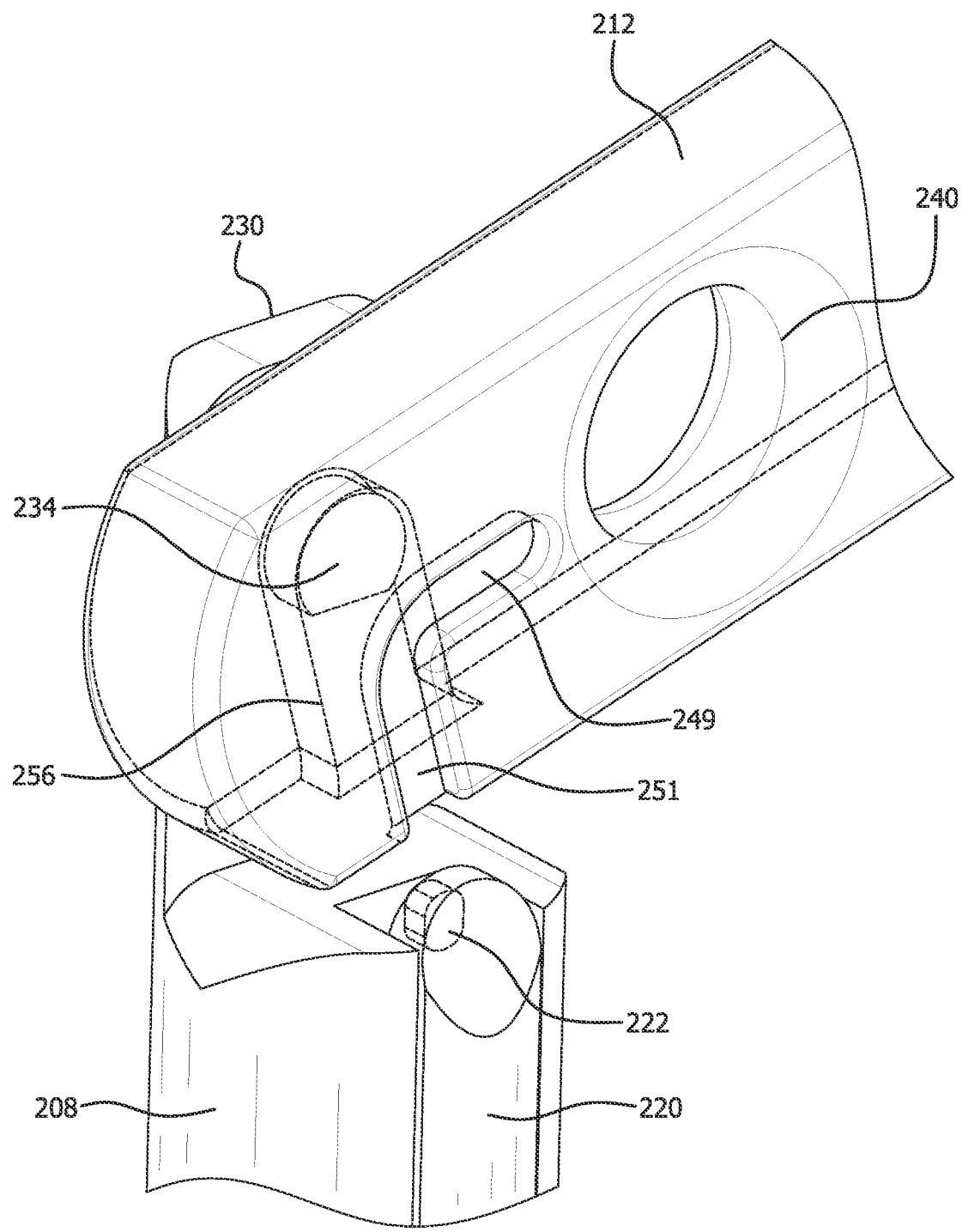
FIG. 27D is in the fourth mode of operation.
Figure 27E:
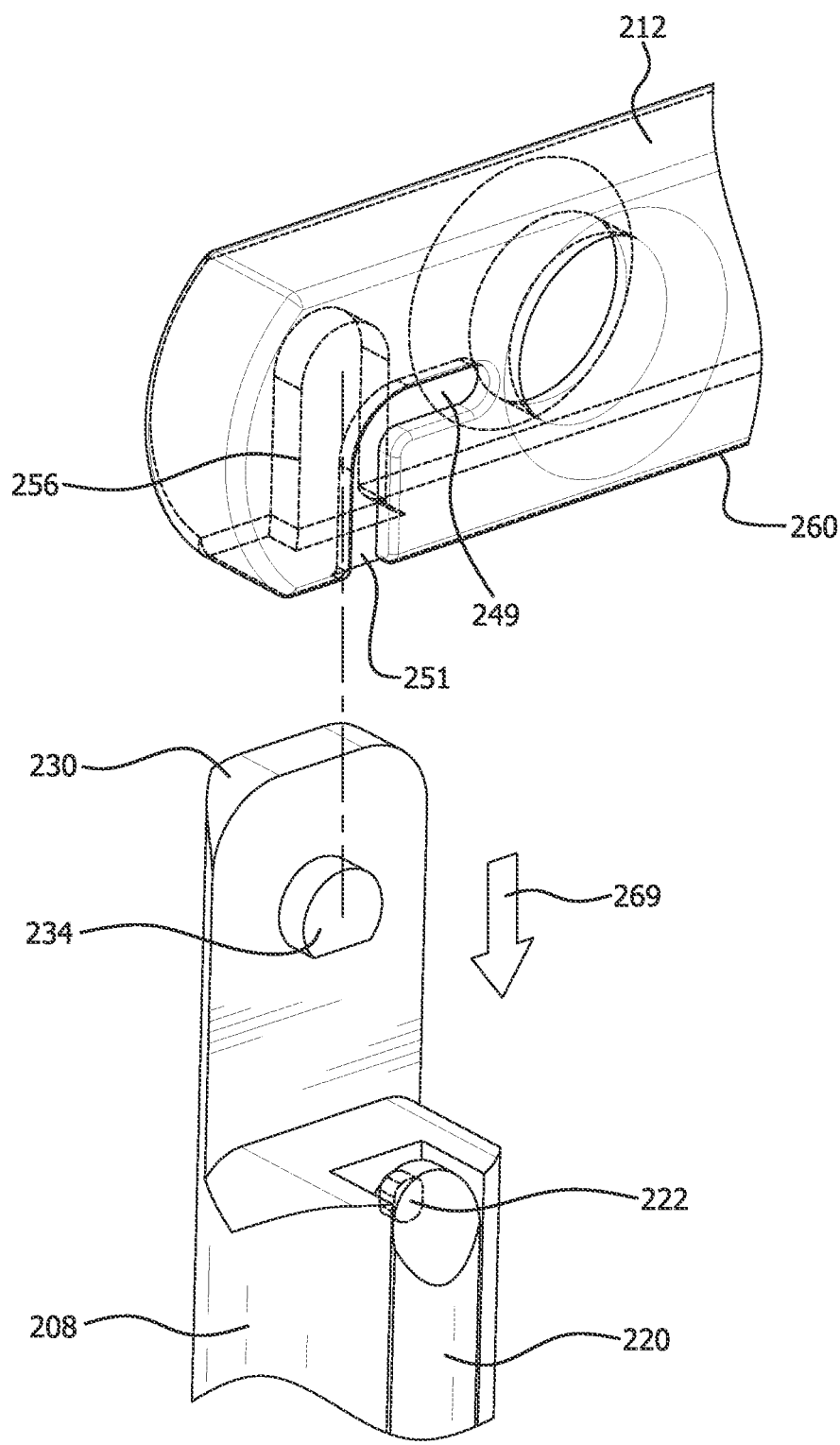
FIG. 27E is in the fifth mode of operation.

Operation of the device can begin as by operating the actuator button 18 as previously described, which will cause proximal movement of the actuator shaft 216. This will cause axial and proximal movement of the engagement projection 220 and the cam protrusion 222 (FIG. 26B, FIG. 27B). The cam protrusion 222 will strike curved portion 253 of the curved groove 248 which will result in rotation of the surgical button 212 as shown by arrow 261. Continued proximal and axial movement of the engagement projection 220 and the cam protrusion 222 will further rotate the surgical button 212 (FIG. 26C, FIG. 27C). The cam protrusion 222 will exit the laterally extending portion 251 of the curved groove 248 at the elongated side face 260. The engagement projection 220 will continue axial and proximal movement until it is removed from the laterally extending groove portion 251, and fully retracted within the inserter head 208 (FIG. 26D, FIG. 27D). The axis of the surgical button 212 at this position can be at substantially a right angle to its starting position. The inserter head 208 can then be removed and the movable protrusion 234 will slide from transverse groove 256 at the elongated side face 260 as shown by arrow 265 (FIG. 26E, FIG. 27E). The button inserter device 200 can then be removed from the patient and the surgical button 212 as indicated by arrows 265 and 269 and can be manipulated as desired by the surgeon.

The invention as shown in the drawings and described in detail herein disclose arrangements of elements of particular construction and configuration for illustrating preferred embodiments of structure and method of operation of the present invention. It is to be understood however, that elements of different construction and configuration and other arrangements thereof, other than those illustrated and described may be employed in accordance with the spirit of the invention, and such changes, alternations and modifications as would occur to those skilled in the art are considered to be within the scope of this invention as broadly defined in the appended claims. In addition, it is to be understood that the phraseology and terminology employed herein are for the purpose of description and should not be regarded as limiting.

We claim:

1. A surgical button, comprising a button body with opposing first and second button body faces, and button body sides comprising elongated sides and short sides, and comprising at least two suture openings extending through the button body from the first button body face to the second button body face, the surgical button further comprising a first engagement depression comprising at least one elongated engagement groove on the first button body face for axially receiving a first engagement protrusion of a button inserter device, the engagement groove extending from a laterally inward location on the first button body face to one of the button body sides, and a second engagement depression in the second button body face and spaced from the button body sides for engagement of a second engagement protrusion on an inserter device.

2. The surgical button of claim 1, wherein the elongated engagement groove is medially positioned on the first button body face and parallel to one of the elongated sides of the button body and extends to a short side of the button body.

3. The surgical button of claim 1, wherein the second engagement depression is at least a third opening extending through the button body perpendicularly to the button body faces and overlapping the elongated engagement groove.

4. The surgical button of claim 1, wherein the elongated engagement groove comprises a curved portion and extends longitudinally and then transversely to a first of the button body elongated sides.

5. The surgical button of claim 4, further comprising a second engagement depression on the second of the opposing button body faces for engagement of a second protrusion on an inserter device.

6. The surgical button of claim 5, wherein the second engagement depression comprises a transverse groove extending perpendicularly to and intersecting with the first button body elongated side.

7. The surgical button of claim 4, wherein the elongated engagement groove comprises a first straight portion extending longitudinally and parallel to the first button body elongated side to the curved portion, and a second straight portion extending transversely from the curved portion to the first button body elongated side.

8. The surgical button of claim 7, further comprising a second engagement depression on the second of the opposing button body faces for engagement a second protrusion on an inserter device, the second engagement depression comprising a transverse groove extending perpendicularly to and intersecting with the first button body elongated side.

9. The surgical button of claim 8, wherein the short sides of the surgical button define proximal and distal ends of the surgical button, and the elongated engagement groove and the second engagement depression are provided adjacent the proximal end.

10. The surgical button of claim 1, wherein the short sides of the surgical button comprises proximal and distal ends, and the engagement groove is provided adjacent the proximal end.

11. The surgical button of claim 1, further comprising a manipulation opening at an axial end of the surgical button opposite the second engagement depression.

* * * * *